United States Patent
He et al.

(10) Patent No.: US 9,487,499 B2
(45) Date of Patent: Nov. 8, 2016

(54) METHODS OF MAKING FUSED RING COMPOUNDS

(71) Applicant: Transitions Optical, Inc., Pinellas Park, FL (US)

(72) Inventors: Meng He, Palm Harbor, FL (US); Anil Kumar, Murrysville, PA (US)

(73) Assignee: Transitions Optical, Inc., Pinellas Park, FL (US)

( * ) Notice: Subject to any disclaimer, the term of this patent is extended or adjusted under 35 U.S.C. 154(b) by 0 days.

(21) Appl. No.: 14/822,938

(22) Filed: Aug. 11, 2015

(65) Prior Publication Data
US 2015/0336922 A1    Nov. 26, 2015

Related U.S. Application Data

(62) Division of application No. 13/314,735, filed on Dec. 8, 2011, now Pat. No. 9,139,571.

(60) Provisional application No. 61/459,613, filed on Dec. 16, 2010.

(51) Int. Cl.
| | |
|---|---|
| *C07D 405/04* | (2006.01) |
| *C07D 407/04* | (2006.01) |
| *C07D 311/94* | (2006.01) |
| *C07C 37/11* | (2006.01) |
| *C07C 41/01* | (2006.01) |
| *C07C 51/353* | (2006.01) |

(52) U.S. Cl.
CPC ............. *C07D 311/94* (2013.01); *C07C 37/11* (2013.01); *C07C 41/01* (2013.01); *C07C 51/353* (2013.01); *C07D 405/04* (2013.01); *C07D 407/04* (2013.01); *C07C 2102/08* (2013.01); *C07C 2103/40* (2013.01)

(58) Field of Classification Search
CPC   C07D 405/04; C07D 407/04; C07D 311/94; C07C 37/11; C07C 41/01; C07C 51/353
See application file for complete search history.

(56) References Cited

U.S. PATENT DOCUMENTS

| | | | |
|---|---|---|---|
| 3,361,706 A | 1/1968 | Smith et al. | |
| 3,562,172 A | 2/1971 | Ono et al. | |
| 3,567,605 A | 3/1971 | Becker | |
| 3,578,602 A | 5/1971 | Ono et al. | |
| 4,215,010 A | 7/1980 | Hovey et al. | |
| 4,342,668 A | 8/1982 | Hovey et al. | |
| 4,637,698 A | 1/1987 | Kwak et al. | |
| 4,816,584 A | 3/1989 | Kwak et al. | |
| 4,818,096 A | 4/1989 | Heller et al. | |
| 4,826,977 A | 5/1989 | Heller et al. | |
| 4,880,667 A | 11/1989 | Welch | |
| 4,931,219 A | 6/1990 | Kwiatkowski et al. | |
| 4,931,220 A | 6/1990 | Haynes et al. | |
| 5,066,818 A | 11/1991 | Gemert et al. | |
| 5,238,931 A | 8/1993 | Yoshikawa et al. | |
| 5,274,132 A | 12/1993 | VanGemert | |
| 5,384,077 A | 1/1995 | Knowles | |
| 5,405,958 A | 4/1995 | VanGemert | |
| 5,466,398 A | 11/1995 | VanGemert et al. | |
| 6,068,797 A | 5/2000 | Hunt | |
| 6,225,466 B1 | 5/2001 | Mann et al. | |
| 6,555,028 B2 | 4/2003 | Walters et al. | |
| 7,262,295 B2 | 8/2007 | Walters et al. | |
| 8,698,117 B2 * | 4/2014 | He | C07D 311/92 250/586 |
| 2009/0323011 A1 | 12/2009 | He et al. | |

OTHER PUBLICATIONS

Blumenkopf et al., "Vinylsilane- and Alkynylsilane-Terminated Cyclization Reactions", Chemical Reviews, 1986, pp. 857-873, vol. 86.
Cahiez et al., "Chemistry of Organomanganese(II) Compounds", Chemical Reviews, 2009, pp. 1434-1475, vol. 109.
Gabbutt et al., "Synthesis and photochromic properties of substituted 3H-naptho[2,1-b]pyrans", Tetrahedron, 2005, pp. 463-471, vol. 61.
Galatsis et al., "Indenone synthesis. Improved synthetic protocol and effect of substitution on the intramolecular Friedel-Crafts acylation", Canadian Journal of Chemistry, 1994, pp. 1656-1659, vol. 72.
Hawley's Condensed Chemical Dictionary, 1997, Thirteenth Edition, pp. 901-902, John Wiley & Sons.
Ishikawa et al., "Novel Carbon—Carbon Bond-Forming Reactions Using Carbocations Produced from Substituted Propargyl Silyl Ethers by the Action of TMSOTf", Journal of Organic Chemistry, 2001, pp. 4635-4642, vol. 66.
Van Gemert, "Benzo and Naphthopyrans (Chromenes)", Organic Photochromic and Thermochromic compounds, 1999, pp. 111-140, vol. 1, Chapter 3, Plenum Press, New York.

* cited by examiner

*Primary Examiner* — Sun Jae Yoo
(74) *Attorney, Agent, or Firm* — The Webb Law Firm

(57) ABSTRACT

The present invention relates to methods of making fused ring compounds, such as indeno-fused naphthols, and fused ring indenopyran compounds, such as indeno-fused naphthopyrans, that each employ an unsaturated compound represented by the following Formula II.

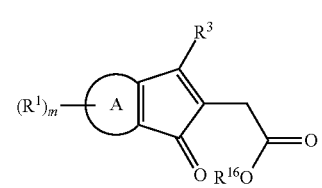

Referring to the unsaturated compound of Formula II: Ring-A can be selected from optionally substituted aryl (e.g., phenyl); m can be, for example, from 0 to 4; $R^1$ for each m can be selected from optionally substituted hydrocarbyl (e.g., $C_1$-$C_6$ alkyl) optionally interrupted with at least one linking group (e.g., —O—); and $R^3$ and $R^{16}$ can each be independently selected from, for example, hydrogen or optionally substituted hydrocarbyl, such as $C_1$-$C_8$ alkyl. When Ring-A is a phenyl group, the unsaturated compound represented by Formula II can be referred to as an unsaturated indanone acid/ester compound, or an indenone acid/ester compound (depending on whether $R^{16}$ is hydrogen, or an optionally substituted hydrocarbyl group).

5 Claims, No Drawings

METHODS OF MAKING FUSED RING COMPOUNDS

CROSS REFERENCE TO RELATED APPLICATIONS

This application is entitled to and claims the benefit of U.S. patent application Ser. No. 13/314,735, filed on Dec. 8, 2011, which is entitled to and claims the benefit of U.S. Provisional Patent Application No. 61/459,613, filed on Dec. 16, 2010, the disclosures of which are each incorporated herein by reference in their entirety.

FIELD OF THE INVENTION

The present invention relates to methods of making fused ring compounds and fused ring indenopyran compounds that each involve the use of certain unsaturated compounds.

BACKGROUND OF THE INVENTION

Indeno-fused ring compounds, such as A and B ring fused inden-6-ol compounds, have many uses, such as intermediates in the synthesis of photochromic compounds and materials, such as indeno-fused ring pyran compounds, including A and B ring fused indenopyran compounds. Photochromic materials, such as indeno-fused naphthopyrans, in response to certain wavelengths of electromagnetic radiation (or "actinic radiation"), typically undergo a transformation from one form or state to another form, with each form having a characteristic or distinguishable absorption spectrum associated therewith. Typically, upon exposure to actinic radiation, many photochromic materials are transformed from a closed-form, which corresponds to an unactivated (or bleached, e.g., substantially colorless) state of the photochromic material, to an open-form, which corresponds to an activated (or colored) state of the photochromic material. In the absence of exposure to actinic radiation, such photochromic materials are reversibly transformed from the activated (or colored) state, back to the unactivated (or bleached) state. Compositions and articles, such as eyewear lenses, that contain photochromic materials or have photochromic materials applied thereto (e.g., in form of a photochromic coating composition) typically display colorless (e.g., clear) and colored states that correspond to the colorless and colored states of the photochromic materials contained therein or applied thereto.

Indeno-fused naphthol materials such as A and B ring fused inden-6-ol compounds are typically prepared by a synthetic scheme involving the reaction of a benzophenone with a dialkyl succinate, which is typically referred to as a Stobbe reaction route. When unsymmetrical benzophenones are used, a mixture of indeno-fused naphthol materials typically results from the Stobbe reaction route. The mixture of indeno-fused naphthols typically must be separated so as to isolate the desired indeno-fused naphthol. The isolated indeno-fused naphthol can then be used in subsequent reactions (e.g., in the synthesis of photochromic indeno-fused naphthopyrans). The separation and isolation steps generally result in significantly reduced yields relative to the desired indeno-fused naphthol materials.

Some photochromic materials, such as photochromic indeno-fused naphthopyrans can be expensive, and in light of economic considerations, reducing the costs associated with synthesizing such materials is typically desirable.

It would be desirable to develop new materials, such as intermediates, and new methods of using such newly developed materials, to make, for example, indeno-fused naphthols and related materials. In addition, it would be desirable that such newly developed materials and methods provide improvements, such as, higher yields, a reduced number of synthetic steps, and reduced costs relative to previous synthetic methods.

SUMMARY OF THE INVENTION

In accordance with the present invention, there is provided a method of forming an indeno-fused ring compound, such as an A and B ring fused inden-6-ol compound, represented by the following Formula I,

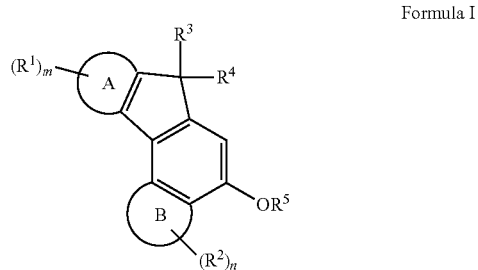

Formula I

With reference to Formula I, Ring-A and Ring-B are each independently selected from unsubstituted aryl, substituted aryl, unsubstituted fused ring aryl, substituted fused ring aryl, unsubstituted heteroaryl, and substituted heteroaryl.

With further reference to Formula I, m and n are each independently selected from 0 to a value corresponding to as many positions on Ring-A and Ring-B, respectively, to which an $R^1$ group or an $R^2$ group can be bonded. With some embodiments, m and n are each independently 0 to 4. Ring-A positions to which an $R^1$ group is not bonded, can instead have hydrogen groups bonded thereto. Similarly, Ring-B positions to which an $R^2$ group is not bonded, can instead have hydrogen groups bonded thereto.

In addition, $R^1$ for each m, and $R^2$ for each n, are in each case independently selected from: hydrocarbyl optionally interrupted with at least one of —O—, —S—, —C(O)—, —C(O)O—, —S(O)—, —SO$_2$—, —N=N—, —N(R$_{11}$')— where $R_{11}'$ is selected from hydrogen, hydrocarbyl or substituted hydrocarbyl, —Si(OR$_{13}$')$_k$(R$_{13}$')$_j$—, where k and j are each independently selected from 0 to 2, provided that the sum of k and j is 2, and each $R_{13}'$ is independently selected from hydrogen, hydrocarbyl and substituted hydrocarbyl, and combinations of two or more thereof; substituted hydrocarbyl optionally interrupted with at least one of —O—, —S—, —C(O)—, —C(O)O—, —S(O)—, —SO$_2$—, —N=N—, —N(R$_{11}$')— where $R_{11}'$ is selected from hydrogen, hydrocarbyl or substituted hydrocarbyl, —Si(OR$_{13}$')$_k$(R$_{13}$')$_j$—, where k and j are each independently selected from 0 to 2, provided that the sum of k and j is 2, and each $R_{13}'$ is independently selected from hydrogen, hydrocarbyl and substituted hydrocarbyl, and combinations of two or more thereof; halogen; cyano; and —N(R$_{11}$')R$_{12}'$, wherein $R_{11}'$ and $R_{12}'$ are each independently selected from hydrogen, hydrocarbyl or substituted hydrocarbyl, or $R_{11}'$ and $R_{12}'$ together form a ring structure optionally including at least one heteroatom.

The $R^3$ and $R^4$ groups of Formula I are each independently selected from: hydrogen; hydrocarbyl optionally interrupted with at least one of —O—, —S—, —C(O)—, —C(O)O—, —S(O)—, —SO$_2$—, —N=N—, and —N($R_{11}'$)— where $R_{11}'$ is selected from hydrogen, hydrocarbyl or substituted hydrocarbyl, and combinations of two or more thereof; and substituted hydrocarbyl optionally interrupted with at least one of —O—, —S—, —C(O)—, —C(O)O—, —S(O)—, —SO$_2$—, —N═N—, and —N($R_{11}'$)— where $R_{11}'$ is selected from hydrogen, hydrocarbyl or substituted hydrocarbyl, and combinations of two or more thereof. With some embodiments, one or more of $R^1$, $R^2$, $R^3$ and $R^4$ can in each case independently represent one or more precursors of those groups as described above and further herein with reference to, for example, Formula I.

The $R^5$ group of Formula I can be selected from hydrogen, —C(O)—$R^{13}$ or —S(O)(O)$R^{13}$, in which $R^{13}$ is hydrocarbyl, or halohydrocarbyl.

The method of making the A and B ring fused inden-6-ol compound represented by Formula I, comprises, reacting an unsaturated compound such as a 2-(5-oxocyclopenta-1,3-dien-1-yl)acetic acid/ester compound, represented by the following Formula II, with (i) a reducing agent defined as being selected from, but not limited to, an organo metal hydride, hydrogen, zinc and/or a mixture thereof. Alternatively, the method of making the compound of Formula I comprises, reacting the unsaturated compound with (ii) a first nucleophile represented by Formula III (i.e., $R^4M^1$). Reaction of either (i) or (ii) with the unsaturated compound results in the formation of a saturated compound, such as the A ring fused 2-(2-oxocyclopenta-3-en-1-yl)acetic acid/ester compound, represented by the following Formula IV,

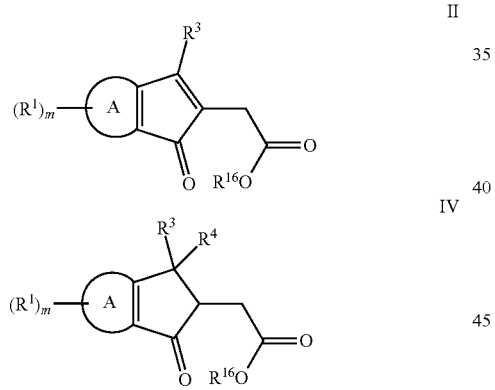

With reference to Formulas II and IV, m, n, $R^1$, $R^2$, $R^3$ and $R^4$ are each as described previously herein with reference to Formula I, or represent precursors of such groups. With reference to Formula III, $R^4$ is a nucleophile of $R^4$ as described with regard to Formula I, and $M^1$ is selected from —Si($R^{18}$)$_3$, where each $R^{18}$ is independently selected from $C_1$-$C_8$ alkyl, or $M^1$ represents a counterion comprising a metal selected from Mg, Li, Mn, Cu, Zn, and combinations thereof. With further reference to Formulas II and IV, $R^{16}$ in each case is independently selected from hydrogen, hydrocarbyl and substituted hydrocarbyl.

The method of making the A and B ring fused inden-6-ol compound represented by Formula I, further comprises, reacting the saturated compound represented by Formula IV with a second nucleophile represented by the following Formula V, thereby forming a substituted intermediate represented by at least one of the following Formulas VI, VII and VIII,

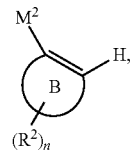

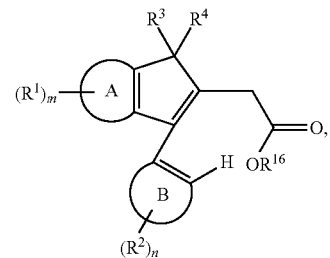

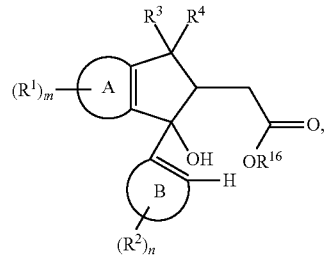

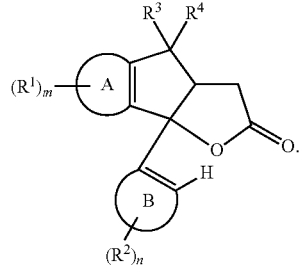

With reference to the second nucleophile represented by Formula V: Ring-B is a nucleophile of Ring-B as described with regard to Formula I; $M^2$ represents a counterion comprising a metal selected from Mg, Li, Mn, Cu, Zn, Ln, and combinations thereof; and m and $R^2$ are each as described previously herein with regard to Formula I, or $R^2$ represents a precursor of such groups as described with reference to Formula I. With reference to the substituted intermediates represented by Formulas VI, VII and VIII, m, n, $R^1$, $R^2$, $R^3$ and $R^4$ are each as described previously herein with reference to Formula I, or represent precursors of such groups.

The method of making the A and B ring fused inden-6-ol compound represented by Formula I, further comprises, converting the substituted intermediate represented by at least one of Formulas VI, VII and VIII to the compound represented by Formula I.

In accordance with the present invention, there is further provided a method of making an A and B ring fused indenopyran compound represented by the following Formula XV,

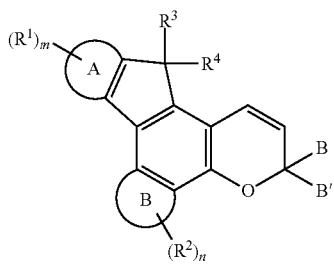

XV

With reference to Formula XV, Ring-A, Ring-B, m, n, $R^1$, $R^2$, $R^3$ and $R^4$ are each as previously described herein, for example, with regard to the indeno-fused ring compound represented by Formula I. Alternatively, one or more of $R^1$, $R^2$, $R^3$ and $R^4$ can in each case independently represent one or more precursors of the those groups as described above and further herein with reference to, for example, Formula I.

The B and B' groups of the compound represented by Formula XV are each independently selected from unsubstituted aryl, substituted aryl, unsubstituted heteroaryl, substituted heteroaryl, polyalkoxy, and polyalkoxy having a polymerizable group. Alternatively B and B', of Formula X, taken together can form a ring structure selected from unsubstituted fluoren-9-ylidene, substituted fluoren-9-ylidene, saturated spiro-monocyclic hydrocarbon ring, saturated spiro-bicyclic hydrocarbon ring, and spiro-tricyclic hydrocarbon ring.

The method of forming the compound represented by Formula XV comprises, reacting an unsaturated compound represented by Formula II, with (i) a reducing agent or (ii) a first nucleophile represented by Formula III, thereby forming a saturated compound represented by Formula IV, each as described previously herein. The method further comprises, reacting the saturated compound represented by Formula IV with a second nucleophile represented by Formula V, which results in the formation of a substituted intermediate represented by at least one of Formulas VI, VII and VIII, each as described previously herein. The substituted intermediate represented by at least one of Formulas VI, VII and VIII, is next converted to an indeno-fused ring compound represented by Formula I, as described previously herein.

The method of forming the compound represented by Formula XV further comprises, reacting compound represented by Formula I with a propargyl alcohol represented by the following Formula XVI, which results in formation of the compound represented by Formula XV,

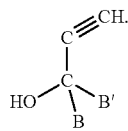

XVI

The B and B' groups of the propargyl alcohol represented by Formula XVI, are each as described previously herein with regard to the compound represented by Formula XV. Alternatively, one or more of the B and B' groups of Formula XVI, can in each case independently represent one or more precursors of the those groups as described above and further herein with reference to, for example, Formula XV.

There is further provided in accordance with the present invention, an unsaturated compound represented by Formula II, as described previously herein. The unsaturated compound represented by Formula II, can be further described and referred to herein as an A-ring fused 2-(5-oxocyclopenta-1,3-dien-1-yl)acetic acid/ester compound.

As used herein and in the claims, the term "actinic radiation" means electromagnetic radiation that is capable of transforming a photochromic material from one form or state to another.

As used herein and in the claims, the term "photochromic" means having an absorption spectrum for at least visible radiation that varies in response to absorption of at least actinic radiation. Further, as used herein the term "photochromic material" means any substance that is adapted to display photochromic properties, i.e. adapted to have an absorption spectrum for at least visible radiation that varies in response to absorption of at least actinic radiation, and which includes at least one photochromic compound.

As used herein and in the claims, molecular weight values of polymers, such as weight average molecular weights (Mw) and number average molecular weights (Mn), are determined by gel permeation chromatography using appropriate standards, such as polystyrene standards.

As used herein and in the claims, polydispersity index (PDI) values represent a ratio of the weight average molecular weight (Mw) to the number average molecular weight (Mn) of the polymer (i.e., Mw/Mn).

As used herein and in the claims, the term "halo" and similar terms, such as halo group, halogen, and halogen group means F, Cl, Br and/or I, such as fluoro, chloro, bromo and/or iodo.

Unless otherwise indicated, all ranges or ratios disclosed herein are to be understood to encompass any and all subranges or subtatios subsumed therein. For example, a stated range or ratio of "1 to 10" should be considered to include any and all subranges between (and inclusive of) the minimum value of 1 and the maximum value of 10; that is, all subranges or subratios beginning with a minimum value of 1 or more and ending with a maximum value of 10 or less, such as but not limited to, 1 to 6.1, 3.5 to 7.8, and 5.5 to 10.

As used herein and in the claims, the articles "a," "an," and "the" include plural referents unless otherwise expressly and unequivocally limited to one referent.

Other than in the operating examples, or where otherwise indicated, all numbers expressing quantities of ingredients, reaction conditions, and so forth used in the specification and claims are to be under stood as modified in all instances by the term "about."

DETAILED DESCRIPTION OF THE INVENTION

Various groups of the compounds and intermediates described previously and further herein, such as but not limited to the $R^1$, $R^2$, $R^3$ and $R^4$ groups of the A and B ring fused inden-6-ol compounds represented by Formula I, can in each case be independently selected from hydrocarbyl and substituted hydrocarbyl.

As used herein and in the claims the term "hydrocarbyl" and similar terms, such as "hydrocarbyl substituent" and "hydrocarbyl group" means: linear or branched $C_1$-$C_{20}$ alkyl (e.g., linear or branched $C_1$-$C_{10}$ alkyl); linear or branched $C_2$-$C_{20}$ alkenyl (e.g., linear or branched $C_2$-$C_{10}$ alkenyl); linear or branched $C_2$-$C_{20}$ alkynyl (e.g., linear or branched $C_2$-$C_{10}$ alkynyl); $C_3$-$C_{12}$ cycloalkyl (e.g., $C_3$-$C_{10}$ cycloalkyl); $C_3$-$C_{12}$ heterocycloalkyl (having at least one hetero atom in the cyclic ring); $C_5$-$C_{18}$ aryl (including polycyclic aryl groups) (e.g., $C_5$-$C_{10}$ aryl); $C_5$-$C_{18}$ heteroaryl (having at least one hetero atom in the aromatic ring); and $C_8$-$C_{24}$ aralkyl (e.g., $C_6$-$C_{10}$ aralkyl).

Representative alkyl groups include but are not limited to methyl, ethyl, propyl, isopropyl, butyl, isobutyl, sec-butyl, tert-butyl, pentyl, neopentyl, hexyl, heptyl, octyl, nonyl and decyl. Representative alkenyl groups include but are not limited to vinyl, allyl and propenyl. Representative alkynyl groups include but are not limited to ethynyl, 1-propynyl, 2-propynyl, 1-butynyl, and 2-butynyl. Representative cycloalkyl groups include but are not limited to cyclopropyl, cyclobutyl, cyclopentyl, cyclohexyl, and cyclooctyl substituents. Representative heterocycloalkyl groups include but are not limited to tetrahydrofuranyl, tetrahydropyranyl and piperidinyl. Representative aryl groups include but are not limited to phenyl and naphthyl. Representative heteroaryl groups include but are not limited to furanyl, pyranyl and pyridinyl. Representative aralkyl groups include but are not limited to benzyl, and phenethyl.

The term "substituted hydrocarbyl" as used herein and in the claims means a hydrocarbyl group in which at least one hydrogen thereof has been substituted with a group that is other than hydrogen, such as, but not limited to, halo groups, hydroxyl groups, ether groups, thiol groups, thio ether groups, carboxylic acid groups, carboxylic acid ester groups, phosphoric acid groups, phosphoric acid ester groups, sulfonic acid groups, sulfonic acid ester groups, nitro groups, cyano groups, hydrocarbyl groups (e.g., alkyl, alkenyl, alkynyl, cycloalkyl, heterocycloalkyl, aryl, heteroaryl, and aralkyl groups), and amine groups, such as —N($R_{11}'$)($R_{12}'$) where $R_{11}'$ and $R_{12}'$ are each independently selected from hydrogen, hydrocarbyl and substituted hydrocarbyl, or $R_{11}'$ and $R_{12}'$ together form a cyclic ring optionally including at least one heteroatom (e.g., —O— and/or —S—).

The term "substituted hydrocarbyl" is inclusive of halohydrocarbyl (or halo substituted hydrocarbyl) substituents. The term "halohydrocarbyl" as used herein and in the claims, and similar terms, such as halo substituted hydrocarbyl, means that at least one hydrogen atom of the hydrocarbyl (e.g., of the alkyl, alkenyl, alkynyl, cycloalkyl, heterocycloalkyl, aryl, heteroaryl, and aralkyl groups) is replaced with a halogen atom selected from chlorine, bromine, fluorine and iodine. The degree of halogenation can range from at least one hydrogen atom being replaced by a halogen atom (e.g., a fluoromethyl group) to full halogenation (perhalogenation) in which all replaceable hydrogen atoms on the hydrocarbyl group have been replaced by a halogen atom (e.g., trifluoromethyl or perfluoromethyl). Correspondingly, the term "perhalohydrocarbyl group" as used herein and in the claims means a hydrocarbyl group in which all replaceable hydrogens have been replaced with a halogen. Examples of perhalohydrocarbyl groups include, but are not limited to, perhalogenated phenyl groups and perhalogenated alkyl groups.

The hydrocarbyl and substituted hydrocarbyl groups from which various groups and substituents, such as $R^1$, $R^2$, $R^3$ and $R^4$, can each be selected, can in each case be independently and optionally interrupted with at least one of —O—, —S—, —C(O)—, —C(O)O—, —S(O)—, —$SO_2$—, —N═N—, and —N($R_{11}'$)—. As used herein and in the claims, by interrupted with at least one of —O—, —S—, —C(O)—, —C(O)O—, —S(O)—, —$SO_2$—, —N═N—, and —N($R_{11}'$)—, means that at least one carbon of, but less than all of the carbons of, the hydrocarbyl group or substituted hydrocarbyl group, is in each case independently replaced with one of the recited divalent linking groups. The hydrocarbyl and substituted hydrocarbyl groups can be interrupted with two or more of the above recited linking groups, which can be adjacent each other or separated by one or more carbons.

As used herein and in the claims, recitations of "linear or branched" or "linear, branched or cyclic" groups, such as linear or branched alkyl, or linear, branched or cyclic alkyl, are herein understood to include: a methylene group or a methyl group; groups that are linear, such as linear $C_2$-$C_{25}$ alkyl groups; groups that are appropriately branched, such as branched $C_3$-$C_{25}$ alkyl groups; and groups that are appropriately cyclic, such as $C_3$-$C_{25}$ cycloalkyl (or cyclic $C_3$-$C_{25}$ alkyl) groups.

As used herein and in the claims, the term "precursor" and related terms, such as "precursors" with regard to the various groups, for example, $R^1$, $R^2$, $R^3$, $R^4$, B and B', of the compounds and intermediates described herein, for example, the indeno-fused ring compounds represented by Formula I, the indeno-fused ring pyran compounds represented by Formula XV, and the unsaturated compounds represented by Formula II, means a group that can be converted in one or more steps to the final or desired group. For purposes of non-limiting illustration: a precursor of a hydroxyl group (—OH) includes, but is not limited to, a carboxylic acid ester group (—OC(O)R where R is hydrogen or an optionally substituted hydrocarbyl); and a precursor of a carboxylic acid ester group (—OC(O)R) includes, but is not limited to, a hydroxyl group (—OH), which can be reacted, for example, with a carboxylic acid halide, such as acetic acid chloride (or acetyl chloride).

As used herein and in the claims, unless otherwise indicated, left-to-right representations of linking groups, such as divalent linking groups, are inclusive of other appropriate orientations, such as, right-to-left orientations. For purposes of non-limiting illustration, the left-to-right representation of the divalent linking group —C(O)O—, is inclusive of the right-to-left representation thereof, —O(O)C—.

The unsaturated compound represented by Formula II of the present invention, and which can be used in the methods of the present invention, can be prepared by appropriate methods. With some embodiments of the present invention, the unsaturated compound represented by Formula II can be prepared by a reaction between a Ring-A $R^3$ ketone and a succinic acid diester, as represented by the following Scheme-1.

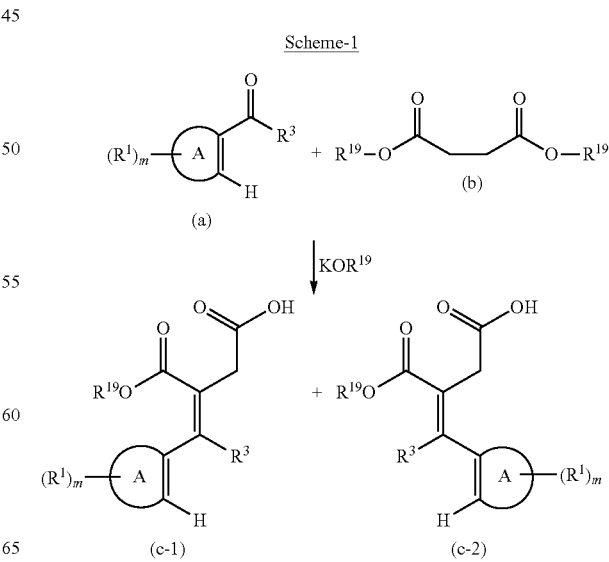

With reference to Scheme-1, the Ring-A $R^3$ ketone (a) is reacted with a succinic acid diester (b), in which each $R^{19}$ is an optionally substituted hydrocarbyl groups, such as an alkyl group (e.g., each $R^{19}$ can be ethyl), in the presence of a strong base, such as an alkali metal alkoxide, such as $NaOR^{19}$ (e.g., sodium ethoxide), or $KOR^{19}$ (e.g., potassium t-butoxide) The reaction of Scheme-1 is conducted under appropriate conditions, such as at a temperature of from 0° C. to 110° C., under an inert atmosphere, and in the presence of an appropriate solvent, such as toluene. The resulting intermediate material (not shown) is washed with one or more protonic acids, such as dilute aqueous hydrochloric acid. This workup of the reaction is described in further detail in the Examples. The reaction represented by Scheme-1 results in the formation of acid-ester intermediates represented by Formulas (c-1) and (c-2). The acid-ester intermediates can be converted into di-acids in aqueous base.

The di-acid or acid-ester intermediates represented by Formulas (c-1) and (c-2) of Scheme-1, can be converted to succinic anhydride intermediates, as represented by the following Scheme-2.

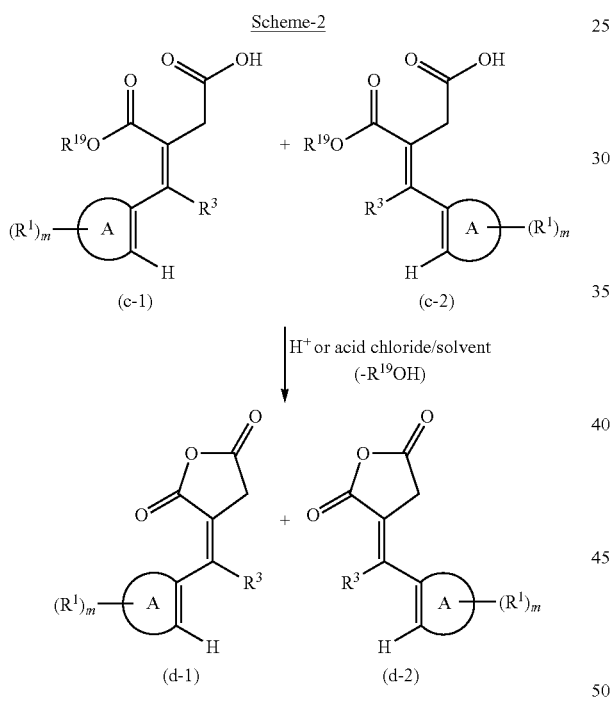

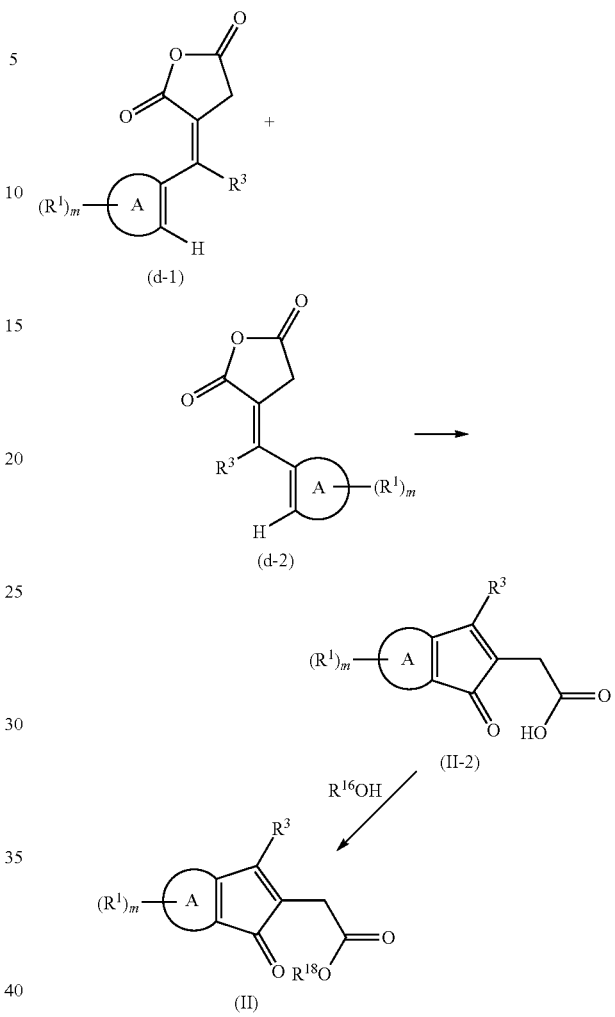

With reference to Scheme-2, the intermediates represented by Formulas (c-1) and (c-2) are converted to the succinic anhydride intermediates represented by Formulas (d-1) and (d-2) in the presence of a protonic acid, such as dodecyclbezene sulfonic acid (DDBSA), with concurrent removal of alcohol ($R^{19}OH$) or water when $R^{19}$ is hydrogen. The conversion represented by Scheme-2 is typically conducted under conditions of elevated temperature, such as at the refluxing temperature of the solvent in the presence of a suitable solvent, such as toluene, with the use of a Dean-Stark trap for water removal. Acid chloride can also be used to make the anhydride.

The succinic anhydride intermediates represented by Formulas (d-1) and (d-2) can next be converted to the unsaturated compound represented by Formula II-2 and II, as represented by the following Scheme-3.

With reference to Scheme-3, the conversion of the succinic anhydride intermediates represented by Formulas (d-1) and (d-2) to the unsaturated compounds represented by Formulas II-2 and II, can be conducted in the presence of a Lewis acid. Examples of Lewis acids include, but are not limited to, aluminum halide, such as aluminum chloride ($AlCl_3$), titanium tetrachloride ($TiCl_4$), tin tetrachloride ($SnCl_4$), boron trifluoride ($BF_3$), and combinations or mixtures thereof. The conversion represented by Scheme-3 is typically conducted in the presence of a suitable solvent, such as methylene chloride, and under appropriate conditions, such as a temperature of from 0° C. to 60° C., and an inert atmosphere (e.g., with a nitrogen sweep). The obtained acid represented by Formula II-a can be used as is for the next reaction or be converted to the ester represented by Formula II and then used.

With some embodiments of the present invention, the method of forming the indeno-fused ring compound represented by Formula I can involve initially reacting the unsaturated compound represented by Formula II with a reducing agent or a first nucleophile represented by Formula III (i.e., $R^4M^1$ as described previously herein), so as to form the saturated compound or intermediate represented by Formula IV, as represented by the following Scheme-4.

Scheme-4

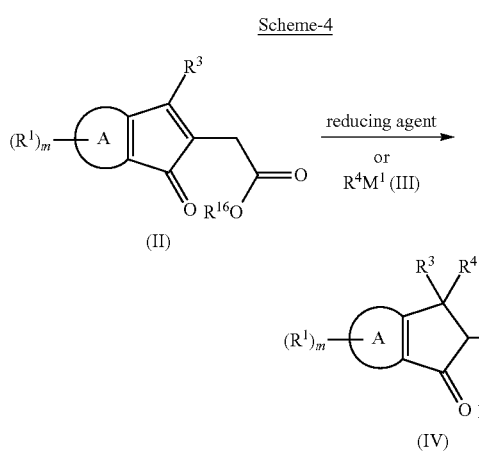

With the reaction represented by Scheme-4, the unsaturated compound represented by Formula II is typically reacted with either a reducing agent or a nucleophile represented by Formula III. The reaction represented by Scheme-4 can be referred to as a 1,4-addition reaction or step. When a reducing agent is used, $R^4$ of the saturated compound represented by Formula IV is typically hydrogen. The metal hydride reducing agent can, in some embodiments, be selected from sodium borohydride and lithium aluminum hydride, or an organo metal hydride reducing agent. The organo metal hydride reducing agent can be one or more di($C_1$-$C_{20}$ alkyl)aluminum hydride reducing agents, such as one or more di($C_1$-$C_6$ alkyl)aluminum hydride reducing agents, e.g., diethyl aluminum hydride and diisobutyl aluminum hydride.

With further reference to the reaction represented by Scheme-4, the reducing agent and the nucleophile represented by Formula III are typically present in at least an equimolar or greater amount relative to the amount of unsaturated compound represented by Formula II. According to some embodiments of the present invention, $M^1$ of Formula III also includes a halogen, and can be represented by $(M^1X)^+$, in which X is a halogen. $M^1$ of Formula III can be selected from $(MgX)^+$, in which X is selected from halogen, such as Cl (e.g., $(MgCl)^+$).

With some embodiments of the present invention, the nucleophile represented by Formula III is a Grignard reagent, and the reaction represented by Scheme-4 is a Grignard reaction, which is conducted under Grignard reaction conditions. Copper (I) halide and manganese chloride typically are added into the Gregnard reaction to facilitate the 1,4-addition reaction as discussed in Chem. Rev. 2009, 109, pp. 1434-1476. The reaction represented by Scheme-4 is typically conducted in the presence of an appropriate solvent, such as tetrahydrofuran (THF), and under conditions of ambient pressure (e.g., approximately 1 atm), under an inert atmosphere (e.g., under a nitrogen sweep). The method of forming the indeno-fused ring compound represented by Formula I, with some embodiments of the present invention, typically next involves reacting the saturated compound represented by Formula IV with a second nucleophile represented by Formula V, so as to result in the formation of at least one substituted intermediate (e.g., Ring-B substituted intermediate) represented by at least one of Formulas VI, VII and VIII, as represented by the following Scheme-5.

Scheme-5

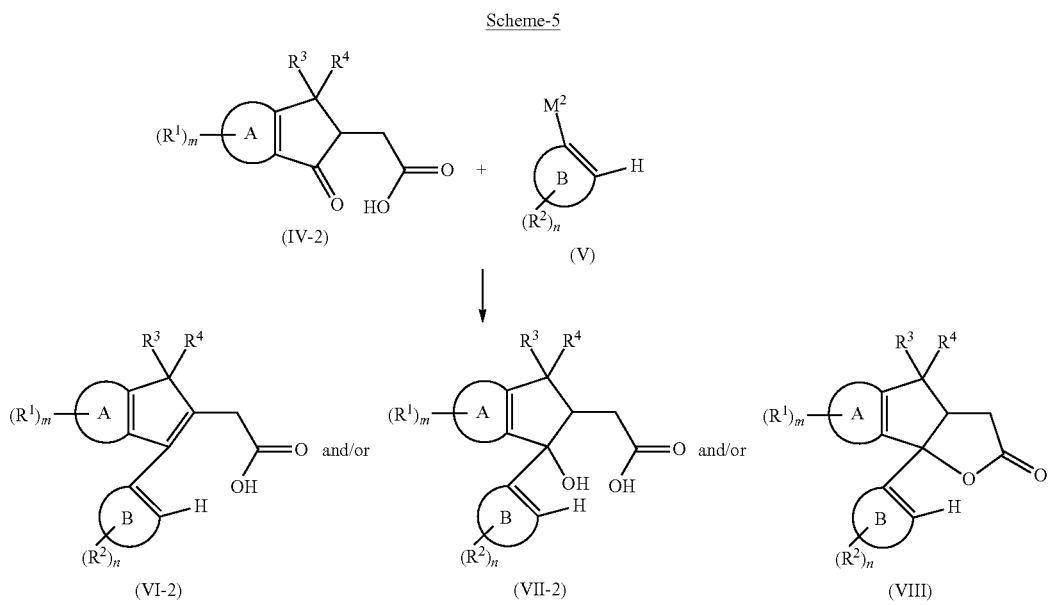

As discussed previously herein, the second nucleophile represented by Formula V, represents a counterion, and in particular a cation, that includes a metal selected from Mg, Li, Mn, Cu, Zn, Ln and combinations of two or more thereof. Typically, the counterion $M^2$ also includes a halogen, and can be represented by $(M^2X)^+$. With some embodiments of the present invention, the counterion $M^2$ includes Mg and a halogen, such as Cl (e.g., $(MgCl)^+$).

With some embodiments of the present invention, the second nucleophile represented by Formula V is a Grignard reagent, and the reaction represented by Scheme-5 is a Grignard reaction, which is conducted under Grignard reaction conditions. The reaction represented by Scheme-5 is typically conducted in the presence of an appropriate solvent, such as tetrahydrofuran (THF), and under conditions of ambient pressure (e.g., approximately 1 atm), under an inert atmosphere (e.g., under a nitrogen sweep), elevated temperature, such as from −20° C. to 65° C., or from −10° C. to 50° C., or from 0° C. to 40° C., and optionally at the refluxing temperature of the solvent.

With further reference to the reaction represented by Scheme-5, the carboxylic acid group of the saturated compound represented by Formula IV typically deactivates a molar equivalent of the second nucleophile represented by Formula V. To address this deactivation, additional second nucleophile represented by Formula V can be added to the reaction vessel. With some embodiments, for every mole of saturated compound represented by Formula IV, two or more moles of second nucleophile represented by Formula V are added to or present within the reaction vessel. With further embodiments of the present invention, when $R^{16}$ is hydrogen, the carboxylic acid group of the saturated compound represented by Formula IV can be protected, for example converted to an oxazoline group, as will be discussed in further detail herein.

When more than one substituted intermediate represented by Formulas VI-2, VII-2 and VIII is formed, for example as represented in Scheme-5, the mixture of such intermediates can optionally be separated and isolated from each other before the next step of the synthesis. Art-recognized separation and isolation methods can be used, such as chromatography. Typically, when more than one substituted intermediate represented by Formulas VI-2, VII-2 and VIII is formed, the mixture of such intermediates is not separated or isolated from each other, and is used as a mixture of intermediates in the next step of the synthesis.

The substituted intermediate represented by at least one of Formulas VI-2, VII-2 and VIII is converted to the compound represented by Formula I, in the next step of the method of the present invention. This conversion can be conducted in substantially one step in the presence of a protonic acid or acid anhydrides and acid chlorides as represented by the following Scheme-6.

When conducted in the presence of a protonic acid, the conversion as represented by Scheme-6 results in the formation of the compound represented by Formula I, in which $R^5$ is hydrogen. The conversion/reaction represented by Scheme-6 is typically conducted under elevated temperature, for example at a temperature from 110° C. to 140° C., or from 120° C. to 135° C., or from 125° C. to 130° C., under conditions of ambient pressure (e.g., approximately 1 atm), and under an inert atmosphere, such as a nitrogen sweep. Examples of protonic acids that can be used in the conversion represented by Scheme-6 include, but are not limited to, carboxylic acids (e.g., acetic, proponoic, and/or butanoic acid), sulfonic acids (e.g., R—S(O)(O)—OH, where R is selected from hydrocarbyl or substituted hydrocarbyl, such as perhalohydrocarbyl), phosphoric acids (e.g., orthophosphoric acid and/or related combinations thereof), and combinations thereof. The protonic acid can be present in an amount ranging from 0.1 molar percent to 2,000 molar percent, i.e., from a catalytic amount to an excess amount, based on 100 molar percent of the starting materials. An excess amount would occur if the protonic acid was used as part of the solvent. e.g. phosphoric acid.

When conducted in the presence of acid anhydride, conversion of the substituted intermediate represented by at least one of Formulas VI-2, VII-2 and VIII to the compound represented by Formula I, is conducted in two steps. Initially an ester intermediate represented by Formula IX is formed, which is then reacted with a protonic acid so as to form the compound represented by Formula I, as represented by the following Scheme-7.

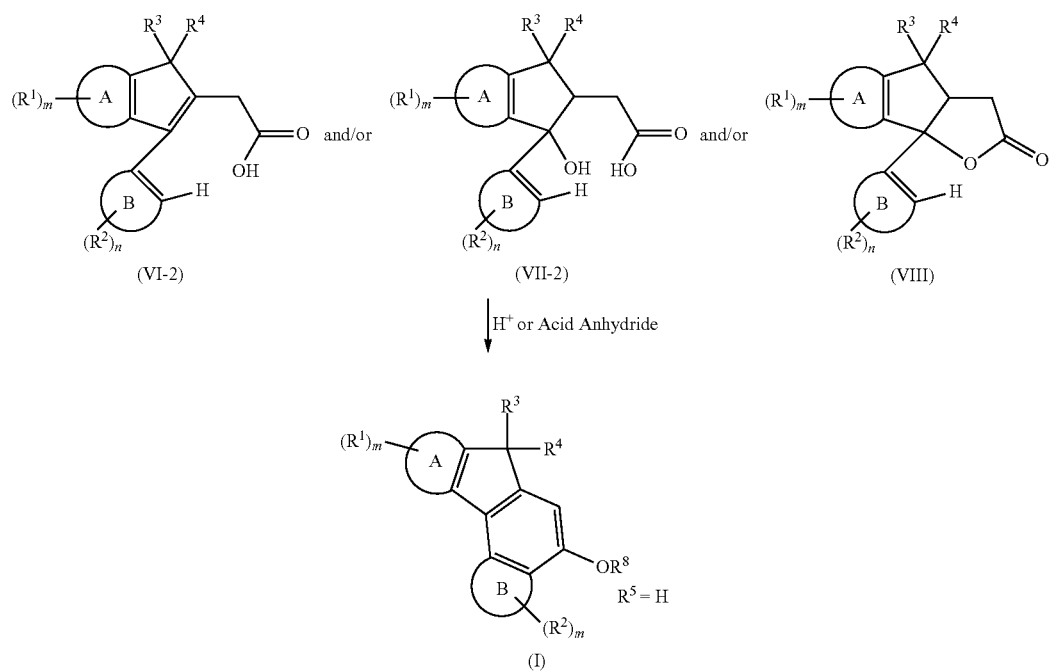

Scheme-6

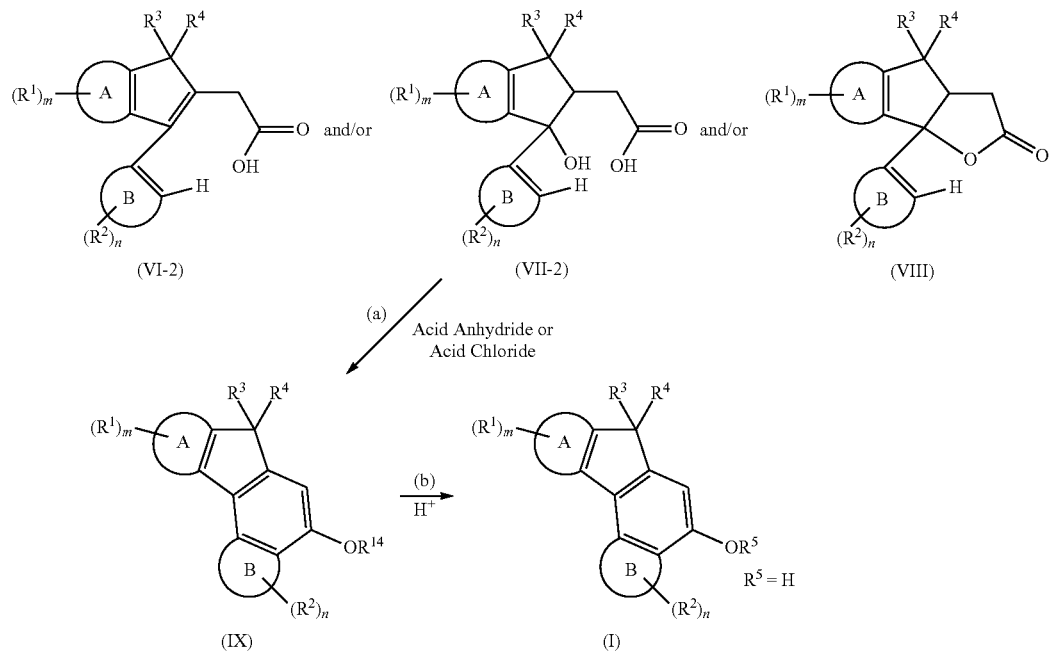

Scheme-7

With reference to Scheme-7, the $R^{14}$ group of the ester intermediate represented by Formula IX is selected from —C(O)—$R^{13}$ and —S(O)(O)$R^{13}$, where $R^{13}$ in each case is independently selected from hydrocarbyl (e.g., $C_1$-$C_{10}$ alkyl) and halohydrocarbyl (e.g., $C_1$-$C_{10}$ perhaloalkyl).

The initial conversion or reaction of step-(a) of Scheme-7, is typically conducted in the presence of a material selected from carboxylic acid halide, carboxylic acid anhydride, sulfonyl halide, sulfonyl anhydride and combinations thereof. The carboxylic acid halide, carboxylic acid anhydride, sulfonyl halide and/or sulfonyl anhydride is typically present in at least an equimolar amount relative to the substituted intermediate represented by at least one of Formulas VI, VII and VIII. Carboxylic acid halides that can be used in step-(a), can be represented by the structure, $R^c$—C(O)—X, where $R^c$ is selected from hydrocarbyl or substituted hydrocarbyl, and X is selected from halogen (e.g., Cl). Sulfonyl halides that can be used in step-(a), can be represented by the formula, $R^d$—S(O)(O)—X, where $R^d$ is selected from hydrocarbyl or substituted hydrocarbyl, and X is selected from halogen (e.g., Cl). Carboxylic acid anhydrides that can be used in step-(a), can be represented by the formula, $R^e$—C(O)—O—C(O)—$R^f$, where $R^e$ and $R^f$ are each independently selected from hydrogen, hydrocarbyl, and substituted hydrocarbyl (e.g., halohydrocarbyl, such as $C_1$-$C_{10}$ perhaloalkyl, e.g., —$CF_3$). Sulfonyl anhydrides that can be used in step-(a), can be represented by the formulas $R^g$—S($O_2$)—O—S($O_2$)—$R^h$, where $R^g$ and $R^h$ are each independently selected from hydrocarbyl or substituted hydrocarbyl.

The ester intermediate represented by Formula IX is converted to the compound represented by Formula I (in which $R^5$ is hydrogen) in step-(b) of Scheme-7 by hydrolysis in the presence of a protonic acid or base. The protonic acid can be selected from hydrogen halides (HX, where X is halogen) such as HCl, sulfonic acids, phosphoric acids, and/or carboxylic acids. Examples of sulfonic acids include, but are not limited to p-toluenesulfonic acid. Examples of phosphoric acids include, but are not limited to phosphoric acid. Examples of carboxylic acids include, but are not limited to trifluoroacetic acid. The base can be selected from sodium hydroxide, potassium hydroxide and potassium carbonate.

The protonic acid or base is typically present in an excess amount relative to the amount of ester intermediate represented by Formula IX. For example the conversion of step-(b) of Scheme-7 can be conducted in the presence of concentrated hydrogen halide acid, such as concentrated HCl, or a base, such as potassium carbonate. The conversion of step-(b) is typically conducted in the presence of a solvent (e.g., methanol), under reflux conditions, for example at a temperature from 65° C. to 150° C., or from 80° C. to 140° C., or from 100° C. to 130° C., under conditions of ambient pressure (e.g., approximately 1 atm), and under an inert atmosphere, such as a nitrogen sweep.

The method of the present invention can result in the formation of indeno-fused ring compounds represented by Formula I in a wide range of yields. For example the method of the present invention can result in the formation of indeno-fused ring compound represented by Formula I in yields of from 1 to 85 mole percent, based on theoretical moles of indeno-fused ring compound that could be produced. Typically, the method of the present invention results in the formation of indeno-fused ring compounds in yields of at least 5 mole percent, such as from 20 to 85 mole percent, or from 30 to 75 mole percent, based on theoretical moles of indeno-fused ring compound that could be produced.

With some embodiments of the present invention, the carboxylic acid group represented by Formula II and IV, can be protected so as to minimize or prevent reaction between the protected carboxylic acid group and the reducing agent or the first nucleophile represented by Formula III. Protection of the carboxylic acid group can also serve to minimize reaction between the carboxylic acid group of the saturated compound represented by Formula IV (when $R^{16}$ is hydrogen) and the second nucleophile represented by Formula V. With some embodiments, the saturated compound represented by Formula IV is converted to an oxazoline protected unsaturated compound represented by the following Formula IIa,

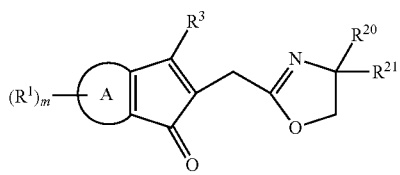

IIa

With reference to the oxazoline protected unsaturated compound represented by Formula IIa, m, $R^1$, $R^3$ and Ring-A are each as described previously herein with regard the unsaturated compound represented by Formula II. Alternatively, $R^1$ and $R^3$ in each case independently represent one or more precursors of the those groups as described above and further herein with reference to, for example Formula II. With further reference to the oxazoline protected unsaturated compound represented by Formula IIa, $R^{20}$ and $R^{21}$ are each independently selected from hydrogen, hydrocarbyl, and substituted hydrocarbyl.

The oxazoline protected unsaturated compound represented by Formula IIa can be formed by suitable methods. With some embodiments, the oxazoline protected unsaturated compound represented by Formula IIa can be formed by reaction of the unsaturated compound represented by Formula II (when $R^{16}$ is hydrogen) with an amino alcohol, such as 2-amino-2-methyl-3-hydroxy propane, as represented by the following Scheme-8.

Scheme-8

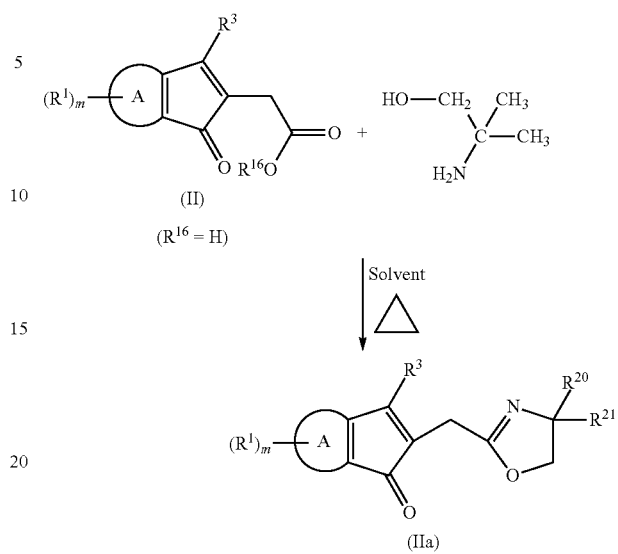

The reaction depicted in Scheme-8 is typically conducted in the presence of a suitable solvent, such as xylene, and under appropriate reflux conditions.

The oxazoline protected unsaturated compound represented by Formula IIa can alternatively be formed by a multi-step synthetic scheme that involves the formation of a carboxylic acid halide intermediate, as represented by the following Scheme-9.

Scheme-9

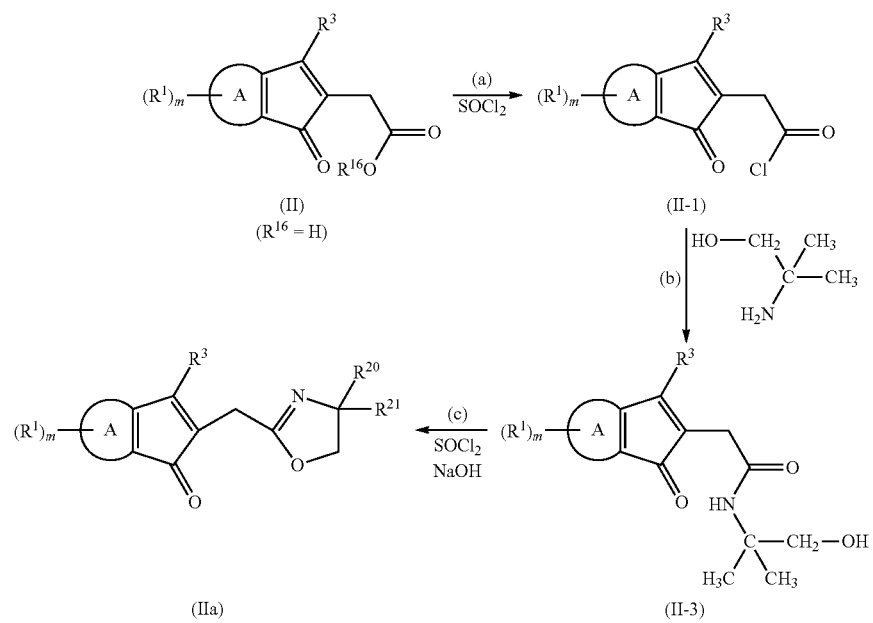

In step-(a) of Scheme-9, thionyl chloride ($SOCl_2$) is reacted with the unsaturated compound represented by Formula II (where $R^{16}$ is hydrogen) under art-recognized conditions, which results in formation of an unsaturated acid chloride intermediate represented by Formula II-1. The unsaturated acid chloride intermediate represented by Formula II-1 is then reacted in step-(b) with an amino alcohol, such as 2-amino-2-methyl-3-hydroxy propane, which results in the formation of the unsaturated hydroxyl functional amide intermediate represented by Formula II-3. In step-(c), the unsaturated hydroxyl functional amide intermediate represented by Formula II-3 is cyclized to form the oxazoline protected unsaturated compound represented by Formula IIa in the presence of thionyl chloride and base, such as sodium hydroxide.

The oxazoline protected unsaturated compound represented by Formula IIa is next reacted with a reducing agent or a first nucleophile represented by Formula III (each as described previously herein), so as to form an oxazoline protected saturated compound represented by Formula IVa.

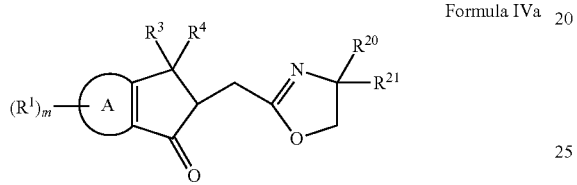

Formula IVa

The reaction of the oxazoline protected unsaturated compound represented by Formula IIa with a reducing agent or a first nucleophile represented by Formula III, so as to form the oxazoline protected saturated compound represented by Formula IVa, can be conducted in accordance with the description provided previously herein with regard to Scheme-4. Typically, however, an excess of organo metal hydride or first nucleophile represented by Formula III, is not required. With some embodiments, a substantially equimolar amount of reducing agent or first nucleophile represented by Formula III is reacted with the oxazoline protected unsaturated compound represented by Formula IIa.

The oxazoline protected saturated compound represented by Formula IVa is then reacted with the second nucleophile represented by Formula V, thereby forming an oxazoline protected substituted intermediate (e.g., an oxazoline protected Ring-B substituted intermediate) represented by at least one of Formula VIa and Formula VIIa,

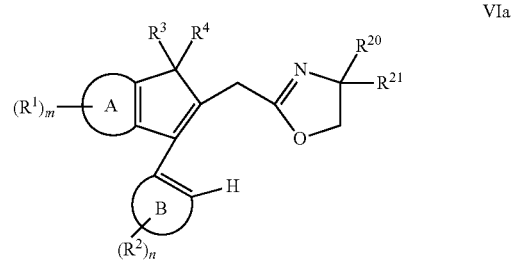

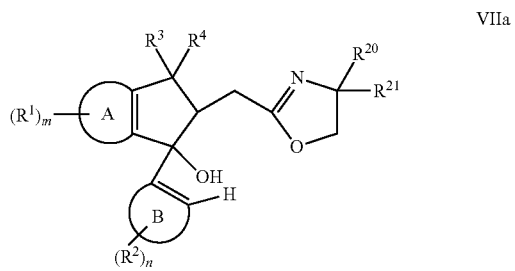

The reaction of oxazoline protected saturated compound represented by Formula IVa with the second nucleophile represented by Formula V, so as to form the oxazoline protected substituted intermediate represented by Formulas VIa and/or VIIa, can be conducted in accordance with the description provided previously herein with regard to Scheme-5. Typically, however, an excess of second nucleophile represented by Formula V, is not required. With some embodiments, a substantially equimolar or greater amount of second nucleophile represented by Formula V is reacted with the oxazoline protected saturated compound represented by Formula IVa.

The oxazoline protected substituted intermediate represented by Formulas VIa and/or VIIb is then converted to the substituted intermediate (e.g., Ring-B substituted intermediate) represented by at least one of Formulas VI-2, VII-2 and VIII. More particularly, the oxazoline group is removed from the oxazoline protected substituted intermediate represented by Formulas VIa and/or VIIb, thus resulting in formation of the substituted intermediate represented by at least one of Formulas VI-2, VII-2 and VIII, as represented by the following Scheme-10.

Scheme-10

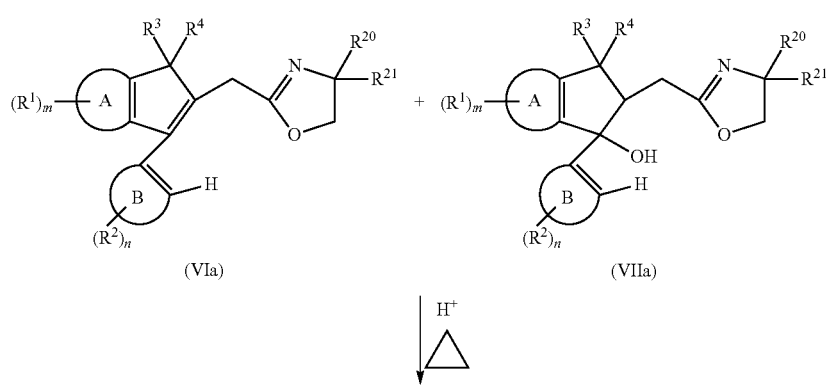

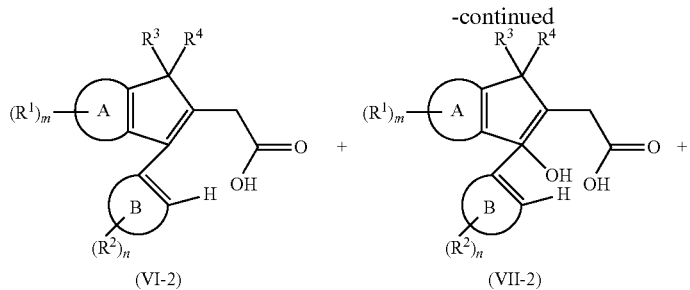
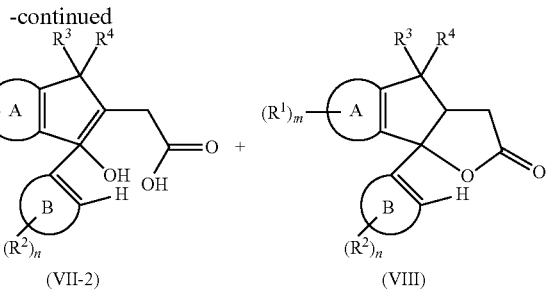

With reference to Scheme-10, removal of the oxazoline group is typically conducted in the presence of a protonic acid, and in particular an inorganic acid, such as concentrated HCl, and under appropriate reflux conditions. Appropriate work-up of the resulting substituted intermediate represented by at least one of Formulas VI-2, VII-2 and VIII is typically conducted, for example to remove the amino alcohol and/or salt thereof.

The compounds prepared by the method of the present invention can be used in numerous applications, such as additives in compositions, or as intermediates in the synthesis of additional compounds, such as non-photochromic (or static) dyes and photochromic dyes. Embodiments of the present invention also include a method of making an A and B ring fused indenopyran compound represented by Formula XV, which involves forming the compound represented by Formula I, as described previously herein, and then reacting the compound represented by Formula I with a propargyl alcohol represented by Formula XVI. Reaction of the compound represented by Formula I and the propargyl alcohol represented by Formula XVI can be represented by the following Scheme-11.

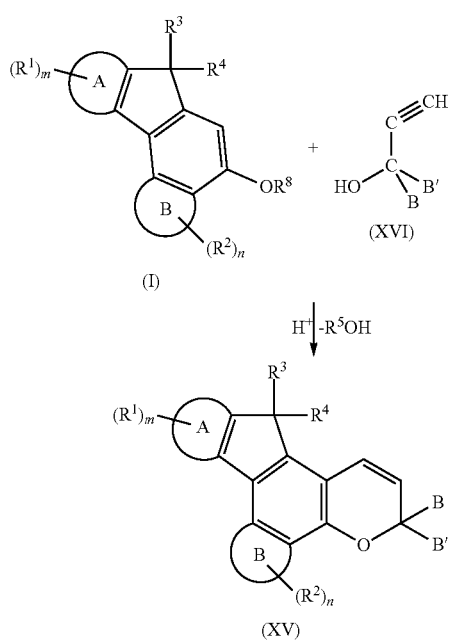

With reference to Scheme-11, when $R^5$ is hydrogen the compound represented by Formula I is reacted or coupled with the propargyl alcohol represented by Formula XVI in the presence of a catalytic amount of a protonic acid, such as dodecyl benzene sulfonic acid (DDBSA) or para-toluene sulfonic acid (pTSA), in a suitable solvent, such as a haloalkyl (e.g., trichloromethane), under an inert atmosphere (e.g., a nitrogen sweep), and at an temperature range, for example, from 25° C. to 110° C., or from 35° C. to 100° C., or from 50° C. to 80° C.

With further reference to Scheme-11, when $R^5$ is $-C(O)-R^{13}$ or $-S(O)(O)R^{13}$, the reaction can include an initial step (not shown) that involves the removal of the $R^5$ group, which typically involves reflux in the presence of a protonic acid, such as hydrochloric acid. The product after hydrolysis is isolated from the reaction mixture before reaction with the propargyl compound.

The groups and substituents of the compounds described previously and further herein, such as the A and B ring fused inden-6-ol compounds (e.g., represented by Formula I), the unsaturated compounds represented by Formula II, the A and B ring fused indenopyran compounds (e.g., represented by Formula XV), and the compounds and intermediates used in their preparation, are described in further detail as follows.

The Ring-A and Ring-B groups of the compounds described herein, such as those compounds represented by Formulas I, II and XV, can in each case be independently selected from unsubstituted aryl, substituted aryl, unsubstituted fused ring aryl, substituted fused ring aryl, unsubstituted heteroaryl, and substituted heteroaryl. The substituents of the substituted aryl, fused ring aryl and heteroaryl groups can each be independently selected from hydrocarbyl groups and substituted hydrocarbyl groups, which each can be optionally interrupted with at least one of $-O-$, $-S-$, $-C(O)-$, $-C(O)O-$, $-S(O)-$, $-SO_2-$, $-N=N-$, and $-N(R_{11}')-$, as described previously herein. Examples of aryl groups from which Ring-A and Ring-B can each be independently selected include, but are not limited to, phenyl and biphenyl. Examples of fused ring aryl groups from which Ring-A and Ring-B can each be independently selected include, but are not limited to, polycyclic aromatic hydrocarbons, such as naphthyl and anthracenyl. Examples of heteroaryl groups from which Ring-A and Ring-B can each be independently selected include, but are not limited to, furanyl, pyranyl and pyridinyl.

With some embodiments of the present invention, $R^1$ for each m, and $R^2$ for each n, are in each case independently selected from: a reactive substituent; a compatiblizing substituent; halogen selected from fluoro and chloro; $C_1$-$C_{20}$ alkyl; $C_3$-$C_{10}$ cycloalkyl; substituted or unsubstituted phenyl; or $-O-R_{10}'$ or $-C(O)-R_{10}'$ or $-C(O)-OR_{10}'$, wherein $R_{10}'$ is hydrogen, $C_1$-$C_{20}$ alkyl, phenyl($C_1$-$C_{20}$) alkyl, mono($C_1$-$C_{20}$)alkyl substituted phenyl($C_1$-$C_{20}$)alkyl, mono($C_1$-$C_{20}$)alkoxy substituted phenyl($C_1$-$C_{20}$)alkyl, ($C_1$-

$C_{20}$)alkoxy($C_2$-$C_{20}$)alkyl, $C_3$-$C_{10}$ cycloalkyl, or mono($C_1$-$C_{20}$)alkyl substituted $C_3$-$C_{10}$ cycloalkyl. The phenyl substituents (i.e., the substituents of the substituted phenyl) can be selected from hydroxyl, halogen, carbonyl, $C_1$-$C_{20}$ alkoxycarbonyl, cyano, halo($C_1$-$C_{20}$)alkyl, $C_1$-$C_{20}$ alkyl or $C_1$-$C_{20}$ alkoxy.

With some further embodiments, $R^1$ for each m, and $R^2$ for each n, are in each case independently and more particularly selected from: $C_1$-$C_6$ alkyl; $C_3$-$C_7$ cycloalkyl; substituted or unsubstituted phenyl; —$OR_{10}'$ or —$OC(=O)R_{10}'$, wherein $R_{10}'$ is hydrogen, $C_1$-$C_6$ alkyl, phenyl($C_1$-$C_3$)alkyl, mono($C_1$-$C_6$)alkyl substituted phenyl($C_1$-$C_3$)alkyl, mono($C_1$-$C_6$)alkoxy substituted phenyl($C_1$-$C_3$)alkyl, ($C_1$-$C_6$)alkoxy($C_2$-$C_4$)alkyl, $C_3$-$C_7$ cycloalkyl, or mono($C_1$-$C_4$)alkyl substituted $C_3$-$C_7$ cycloalkyl. The phenyl substituents (i.e., the substituents of the substituted phenyl) can be more particularly selected from hydroxyl, halogen, carbonyl, $C_1$-$C_6$ alkoxycarbonyl, cyano, halo($C_1$-$C_6$)alkyl, $C_1$-$C_6$ alkyl or $C_1$-$C_6$ alkoxy.

Alternatively or in addition to the previously recited classes and examples, $R^1$ for each m, and $R^2$ for each n, can in each case be independently selected from, —$N(R_{11}')R_{12}'$, wherein $R_{11}'$ and $R_{12}'$ are each independently hydrogen, $C_1$-$C_{20}$ alkyl, phenyl, naphthyl, furanyl, benzofuran-2-yl, benzofuran-3-yl, thienyl, benzothien-2-yl, benzothien-3-yl, dibenzofuranyl, dibenzothienyl, benzopyridyl, fluorenyl, $C_1$-$C_{20}$ alkylaryl, $C_3$-$C_{10}$ cycloalkyl, $C_4$-$C_{20}$ bicycloalkyl, $C_5$-$C_{20}$ tricycloalkyl or $C_1$-$C_{20}$ alkoxyalkyl, wherein said aryl group is phenyl or naphthyl, or $R_{11}'$ and $R_{12}'$ come together with the nitrogen atom to form a $C_3$-$C_{20}$ hetero-bicycloalkyl ring or a $C_4$-$C_{20}$ hetero-tricycloalkyl ring.

Further alternatively or in addition to the previously recited classes and examples, $R^1$ for each m, and $R^2$ for each n, can in each case be independently selected from, a nitrogen containing ring represented by the following graphic Formula XIIA,

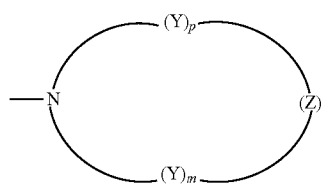

XIIA

With the nitrogen ring substituent represented by general Formula XIIA, each —Y— is independently chosen for each occurrence from —$CH_2$—, —$CH(R_{13}')$—, —$C(R_{13}')_2$—, —CH(aryl)-, —C(aryl)$_2$-, and —$C(R_{13}')$(aryl)-, and Z is —Y—, —O—, —S—, —S(O)—, —$SO_2$—, —NH—, —$N(R_{13}')$—, or —N(aryl)-, wherein each $R_{13}'$ is independently $C_1$-$C_{20}$ alkyl (e.g., $C_1$-$C_6$ alkyl), each aryl is independently phenyl or naphthyl, m is an integer 1, 2 or 3, and p is an integer 0, 1, 2, or 3 and provided that when p is 0, Z is —Y—.

Additionally or alternatively, $R^1$ for each m, and $R^2$ for each n, can in each case also be independently selected from a nitrogen containing ring substituent represented by general formula XIIB and/or general formula XIIC:

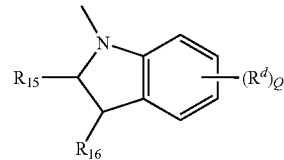

XIIB

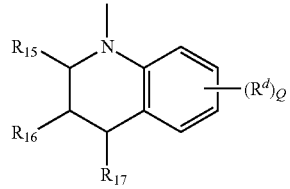

XIIC

For the nitrogen containing ring substituents represented by general formulas XIIB and XIIC, $R_{15}$, $R_{16}$, and $R_{17}$ are each independently hydrogen, $C_1$-$C_{20}$ alkyl (e.g., $C_1$-$C_6$ alkyl), phenyl, or naphthyl, or the groups $R_{15}$ and $R_{16}$ together form a ring of 5 to 8 carbon atoms and each $R^d$ is independently for each occurrence selected from $C_1$-$C_{20}$ alkyl (e.g., $C_1$-$C_6$ alkyl), $C_1$-$C_{20}$ alkoxy (e.g., $C_1$-$C_6$ alkoxy), fluoro or chloro, and Q is an integer 0, 1, 2, or 3.

Further alternatively or additionally, $R^1$ for each m, and $R^2$ for each n, can in each case also be independently selected from, unsubstituted, mono-, or di-substituted $C_4$-$C_{18}$ spirobicyclic amine, or unsubstituted, mono-, and di-substituted $C_4$-$C_{18}$ spirotricyclic amine, wherein the substituents are independently aryl, $C_1$-$C_{20}$ alkyl (e.g., $C_1$-$C_6$ alkyl), $C_1$-$C_{20}$ alkoxy (e.g., $C_1$-$C_6$ alkoxy), or phenyl($C_1$-$C_{20}$)alkyl (e.g., phenyl($C_1$-$C_6$)alkyl).

With some embodiments of the present invention, two adjacent $R^1$ groups, and/or two adjacent $R^2$ groups, can together form a group represented by the following general formula XIID or general formula XIIE,

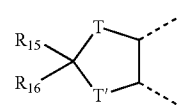

XIID

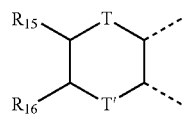

XIIE

With the groups represented by general formulas XIID and XIIE, T and T' are each independently oxygen or the group —$NR_{11}$—, where $R_{11}$, $R_{15}$, and $R_{16}$ are each as set forth and described previously herein.

The $R^3$ and $R^4$ groups, with some embodiments of the present invention, can each be independently selected from: a reactive substituent; a compatiblizing substituent; hydrogen; hydroxy; $C_1$-$C_{20}$ alkyl (e.g., $C_1$-$C_6$ alkyl); $C_1$-$C_{20}$ haloalkyl (e.g., $C_1$-$C_6$ haloalkyl); $C_3$-$C_{10}$ cycloalkyl (e.g., $C_3$-$C_7$ cycloalkyl); allyl; benzyl; or mono-substituted benzyl. The benzyl substituents can be chosen from halogen, $C_1$-$C_{20}$ alkyl (e.g., $C_1$-$C_6$ alkyl) or $C_1$-$C_{20}$ alkoxy (e.g., $C_1$-$C_6$ alkoxy).

The $R^3$ and $R^4$ groups with some further embodiments of the present invention, can each be independently selected from, an unsubstituted, mono- di- or tri-substituted group chosen from phenyl, naphthyl, phenanthryl, pyrenyl, quinolyl, isoquinolyl, benzofuranyl, thienyl, benzothienyl, dibenzofuranyl, dibenzothienyl, carbazolyl, or indolyl. The group substituents can in each case be independently chosen from halogen, $C_1$-$C_{20}$ alkyl (e.g., $C_1$-$C_6$ alkyl) or $C_1$-$C_{20}$ alkoxy (e.g., $C_1$-$C_6$ alkoxy).

The $R^3$ and $R^4$ groups can also, with some embodiments of the present invention, each be independently selected from a mono-substituted phenyl, in which the phenyl has a substituent located at the para position thereof, which is a linking group, —$(CH_2)_t$— or —O—$(CH_2)_t$—, that is connected to an aryl group which is a member of a (or another) photochromic material, such as a naphthopyran, an indeno-fused naphthopyran, or benzopyran, and t is chosen from the integer 1, 2, 3, 4, 5 or 6.

Alternatively, the $R^3$ and $R^4$ groups can each be independently selected from the group —CH($R^{10}$)G, in which $R^{10}$ is hydrogen, $C_1$-$C_{20}$ alkyl (e.g., $C_1$-$C_6$ alkyl) or the unsubstituted, mono- or di-substituted aryl groups phenyl or naphthyl, and G is —$CH_2OR^{11}$, in which $R^{11}$ is hydrogen, —C(O)$R^{10}$, $C_1$-$C_{20}$ alkyl (e.g., $C_1$-$C_6$ alkyl), $C_1$-$C_{20}$ alkoxy($C_1$-$C_{20}$)alkyl (e.g., $C_1$-$C_3$ alkoxy($C_1$-$C_6$)alkyl), phenyl($C_1$-$C_{20}$)alkyl (e.g., phenyl($C_1$-$C_3$)alkyl), mono($C_1$-$C_{20}$)alkoxy substituted phenyl($C_1$-$C_{20}$)alkyl (e.g., mono($C_1$-$C_6$)alkoxy substituted phenyl($C_1$-$C_3$)alkyl), or the unsubstituted, mono- or di-substituted aryl groups phenyl or naphthyl. The substituents of the phenyl and naphthyl groups can each be independently selected from $C_1$-$C_{20}$ alkyl (e.g., $C_1$-$C_6$ alkyl) or $C_1$-$C_{20}$ alkoxy (e.g., $C_1$-$C_6$ alkoxy).

With some embodiments of the present invention, $R^1$ for each m, and $R^2$ for each n, are in each case independently selected from unsubstituted phenyl, substituted phenyl, $C_1$-$C_6$ alkyl, $C_3$-$C_7$ cycloalkyl, $C_1$-$C_8$ haloalkyl, fluoro, chloro, and —O—$R_{10}$'. With further embodiments of the present invention, $R^3$ and $R^4$ are each independently selected from hydrogen, $C_1$-$C_8$ alkyl, $C_1$-$C_8$ haloalkyl, and $C_3$-$C_7$ cycloalkyl.

In accordance with some further embodiments of the present invention, $R^1$ for each m, and $R^2$ for each n, can in each case be independently selected from a group represented by the following Formula XIII, —$(S_1)_c$-$(Q_1$-$(S_2)_d)_d$-$(Q_2$-$(S_3)_e)_e$-$(Q_3$-$(S_4)_f)_f$—$S_5$—P With reference to Formula XIII, $Q_1$, $Q_2$, and $Q_3$ are each independently chosen from, a divalent group chosen from, an unsubstituted or a substituted aromatic group, an unsubstituted or a substituted alicyclic group, an unsubstituted or a substituted heterocyclic group, and mixtures thereof.

The substituents of the substituted aromatic groups, substituted alicyclic groups and substituted heterocyclic groups from which each of $Q_1$, $Q_2$, and $Q_3$ can be selected, are independently chosen from: a group represented by P (as will be described in further detail herein); liquid crystal mesogens; halogen; poly($C_1$-$C_{18}$ alkoxy); $C_1$-$C_{18}$ alkoxycarbonyl; $C_1$-$C_{18}$ alkylcarbonyl; $C_1$-$C_{18}$ alkoxycarbonyloxy; aryloxycarbonyloxy; perfluoro($C_1$-$C_{18}$)alkoxy; perfluoro($C_1$-$C_{18}$)alkoxycarbonyl; perfluoro($C_1$-$C_{18}$)alkylcarbonyl; perfluoro($C_1$-$C_{18}$)alkylamino; di-(perfluoro($C_1$-$C_{18}$)alkyl)amino; perfluoro($C_1$-$C_{18}$)alkylthio; $C_1$-$C_{18}$ alkylthio; $C_1$-$C_{18}$ acetyl; $C_3$-$C_{10}$ cycloalkyl; $C_3$-$C_{10}$ cycloalkoxy; or a straight-chain or branched $C_1$-$C_{18}$ alkyl group that is mono-substituted with cyano, halo, or $C_1$-$C_{18}$ alkoxy, or poly-substituted with halo.

Additionally or alternatively, the substituents of the substituted aromatic groups, substituted alicyclic groups and substituted heterocyclic groups from which each of $Q_1$, $Q_2$, and $Q_3$ can be selected, can be further independently chosen from a group represented by one of the following formulas XIIIA and XIIIB,

With reference to Formulas XIIIA and XIIIB, M is chosen from aluminum, antimony, tantalum, titanium, zirconium and silicon, T is chosen from organofunctional radicals, organofunctional hydrocarbon radicals, aliphatic hydrocarbon radicals and aromatic hydrocarbon radicals, and t is the valence of M.

Liquid crystal mesogens from which each of $Q_1$, $Q_2$, and $Q_3$ can each be independently selected, include but are not limited to art-recognized liquid crystal mesogens. With some embodiments, the liquid crystal mesogens can be selected from those described in United States Patent Application Publication No. US 2009/0323011 A1, see paragraphs [0052] to [0095] and Table 1, the disclosure of which is incorporated herein by reference in their entirety.

With further reference to Formula XIII, the subscripts c, d, e, and f are each independently chosen from an integer ranging from 1 to 20, inclusive of the upper and lower limits (e.g., from 2 to 15, or from 3 to 10).

The $S_1$, $S_2$, $S_3$, $S_4$, and $S_5$ groups of Formula XIII are each independently chose from a spacer unit. The spacer unit can in each case be independently chosen from, —$(CH_2)_g$—, —$(CF_2)_h$—, —$Si(CH_2)_g$—, —$(Si(CH_3)_2O)_h$—, in which g is independently chosen for each occurrence from 1 to 20, and h is a whole number from 1 to 16 inclusive. Alternatively, or additionally, the spacer unit can be independently chosen from —N(Z)—, —C(Z)=C(Z)—, —C(Z)=N—, —C(Z')—C(Z')—, or a single bond, in which Z is independently chosen for each occurrence from hydrogen, $C_1$-$C_{18}$ alkyl, $C_3$-$C_{10}$ cycloalkyl and aryl, and Z' is independently chosen for each occurrence from $C_1$-$C_{18}$ alkyl, $C_3$-$C_{10}$ cycloalkyl and aryl. Further alternatively, or additionally, the spacer unit can be independently chosen from —O—, —C(O)—, —C≡C—, —N=N—, —S—, —S(O)—, —S(O)(O)—, —(O)S(O)O—, —O(O)S(O)O—, or straight-chain or branched $C_1$-$C_{24}$ alkylene residue, said $C_1$-$C_{24}$ alkylene residue being unsubstituted, mono-substituted by cyano or halo, or poly-substituted by halo.

With further reference to Formula XIII: when two spacer units comprising heteroatoms are linked together, the spacer units are linked so that heteroatoms are not directly linked to each other; each bond between $S_1$ and Ring-A and $S_1$ and Ring-B is free of two heteroatoms linked together; and the bond between $S_5$ and P is free of two heteroatoms linked to each other.

The P group of Formula XIII is chosen from, hydroxy, amino, $C_2$-$C_{18}$ alkenyl, $C_2$-$C_{18}$ alkynyl, azido, silyl, siloxy, silylhydride, (tetrahydro-2H-pyran-2-yl)oxy, thio, isocyanato, thioisocyanato, acryloyloxy, methacryloyloxy, 2-(acryloyloxy)ethylcarbamyl, 2-(methacryloyloxy)ethylcarbamyl, aziridinyl, allyloxycarbonyloxy, epoxy, carboxylic acid, carboxylic ester, acryloylamino, methacryloylamino, aminocarbonyl, $C_1$-$C_{18}$ alkyl aminocarbonyl, aminocarbonyl($C_1$-$C_{18}$)alkyl, $C_1$-$C_{18}$ alkyloxycarbonyloxy, halocarbonyl, hydrogen, aryl, hydroxy($C_1$-$C_{18}$)alkyl, $C_1$-$C_{18}$ alkyl, $C_1$-$C_{18}$ alkoxy, amino($C_1$-$C_{18}$)alkyl, $C_1$-$C_{18}$ alkylamino, di-($C_1$-$C_{18}$)alkylamino, $C_1$-$C_{18}$ alkyl($C_1$-$C_{18}$)alkoxy, $C_1$-$C_{18}$ alkoxy($C_1$-$C_{18}$)alkoxy, nitro, poly($C_1$-$C_{18}$)alkyl ether, ($C_1$-$C_{18}$)alkyl($C_1$-$C_{18}$)alkoxy($C_1$-$C_{18}$)alkyl, polyethyleneoxy, polypropyleneoxy, ethylenyl, acryloyl, acryloyloxy($C_1$-$C_{18}$)alkyl, methacryloyl, methacryloyloxy($C_1$-$C_{18}$)alkyl, 2-chloroacryloyl, 2-phenylacryloyl, acryloyloxyphenyl, 2-chloroacryloylamino, 2-phenylacryloylaminocarbonyl, oxetanyl, glycidyl, cyano, isocyanato($C_1$-$C_{18}$)alkyl, itaconic acid ester, vinyl ether, vinyl ester, a styrene derivative, main-chain and side-chain liquid crystal polymers, siloxane derivatives, ethyleneimine derivatives, maleic acid derivatives, fumaric acid derivatives, unsubstituted cinnamic acid derivatives, cinnamic acid derivatives that are substituted with at least one of methyl, methoxy, cyano and halogen, or substituted or unsubstituted chiral or non-chiral monovalent or divalent groups chosen from steroid radicals, terpenoid radicals, alkaloid radicals and mixtures thereof. The substituents of the groups from which P can be selected are independently chosen from $C_1$-$C_{18}$ alkyl, $C_1$-$C_{18}$ alkoxy, amino, $C_3$-$C_{10}$ cycloalkyl, $C_1$-$C_{18}$ alkyl($C_1$-$C_{18}$)alkoxy, fluoro($C_1$-$C_{18}$)alkyl, cyano, cyano($C_1$-$C_{18}$)alkyl, cyano($C_1$-$C_{18}$)alkoxy or mixtures thereof. With some embodiment P can be a structure having from 2 to 4 reactive groups. With further embodiments, P can be an unsubstituted or substituted ring opening metathesis polymerization precursor.

With further reference to Formula XIII, subscripts d', e' and f' are each independently chosen from 0, 1, 2, 3, and 4, provided that the sum of d'+e'+f' is at least 1.

With some embodiments of the present invention. Ring-A and Ring-B are each independently selected from unsubstituted and substituted aryl groups, such as unsubstituted and substituted phenyl groups. Correspondingly, in accordance with some embodiments of the present invention, the compound represented by Formula I, is more particularly represented by the following Formula Ia.

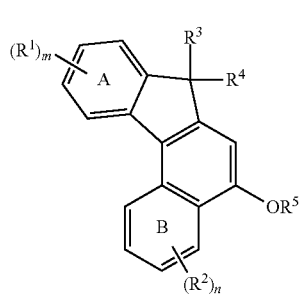

With reference to Formula Ia, m, n, $R^1$, $R^2$, $R^3$, $R^4$ and $R^5$ are each as described previously herein. The compound represented by Formula Ia can be referred to as an indeno-fused naphtho-compound, such as an indeno-fused naphthol (e.g., when $R^5$ is hydrogen).

In accordance with some embodiments of the present invention, the unsaturated compound represented by Formula II, can be represented by the following Formula IIb.

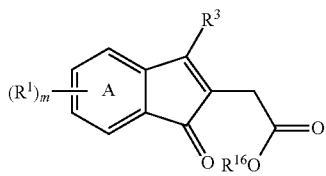

With reference to Formula IIb, m, $R^1$, $R^3$ and $R^{16}$ are each as described previously herein. The unsaturated compound represented by Formula IIb can be referred to as an unsaturated indanone acid/ester compound, or an indenone acid/ester compound (depending on whether $R^{16}$ is hydrogen, or an optionally substituted hydrocarbyl group). With the unsaturated compound represented by Formulas II, IIa (protected with an oxazoline group) or IIb, in some embodiments of the present invention: $R^1$ for each m is independently selected from $C_1$-$C_6$ alkyl, $C_3$-$C_7$ cycloalkyl, $C_1$-$C_8$ haloalkyl, fluoro, chloro, and —O—$R_{10}$'; $R^3$ is selected from hydrogen, $C_1$-$C_5$ alkyl, $C_1$-$C_8$ haloalkyl, and $C_3$-$C_7$ cycloalkyl; and $R^{16}$ is selected from hydrogen and $C_1$-$C_8$ alkyl.

The saturated compound represented by Formula IV, in some embodiments, is represented by the following Formula IVb.

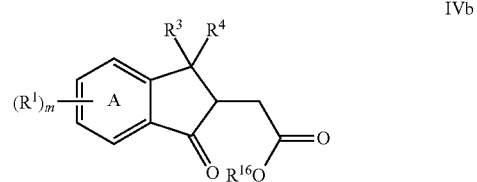

With reference to Formula IVb, m, $R^1$, $R^3$, $R^4$ and $R^{16}$ are each as described previously herein. The saturated compound represented by Formula IVb can be referred to as a saturated indanone acid/ester compound, or an indanone acid/ester compound (depending on whether $R^{16}$ is hydrogen, or an optionally substituted hydrocarbyl group).

The second nucleophile represented by Formula V, in some embodiments, is represented by the following Formula Va.

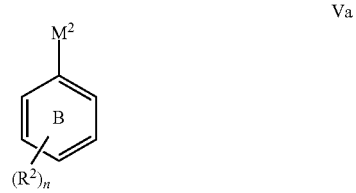

With reference to Formula Va, m, $R^2$ and $M^2$ are each as described previously herein.

The substituted intermediate represented by at least one of Formulas VI, VII and VII, are each in some embodiments represented by the following Formulas VIb, VIIb and VIIb,

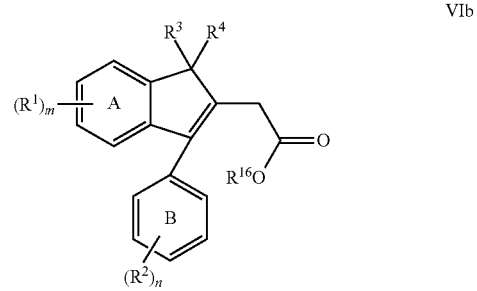

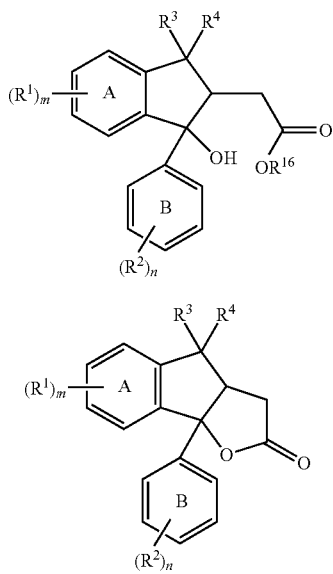

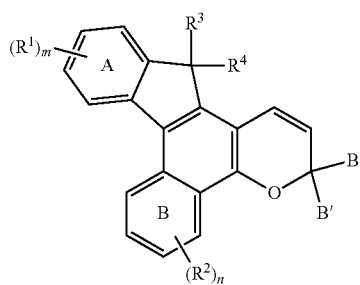

With Formulas VIb, VIIb and VIIIb, m, n, $R^1$, $R^2$, $R^3$ and $R^4$ are each as described previously herein, The A and B ring fused indenopyran compound represented by Formula XV is in some embodiments represented by the following Formula XVa.

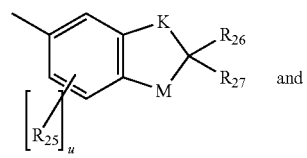

With the indeno-fused ring pyran compound represented by Formula XVa, m, n, $R^1$, $R^2$, $R^3$ and $R^4$ are each as described previously herein. The B and B' groups of the indeno-fused ring pyran compound represented by Formula XVa are each as described previously and further herein. The indeno-fused ring pyran compound represented by Formula XVa can be referred to an indeno-fused naphthopyran compound.

The B and B' groups of, for example, the indeno-fused ring pyran compound represented by Formulas XV and XVa, and the propargyl alcohol represented by Formula XVI, are described in further detail as follows. More particularly, B and B' can each independently be selected from: an aryl group that is mono-substituted with a reactive substituent or a compatiblizing substituent; a substituted phenyl; a substituted aryl; a substituted 9-julolidinyl; a substituted heteroaromatic group chosen from pyridyl, furanyl, benzofuran-2-yl, benzofuran-3-yl, thienyl, benzothien-2-yl, benzothien-3-yl, dibenzofuranyl, dibenzothienyl, carbazoyl, benzopyridyl, indolinyl, and fluorenyl. The phenyl, aryl, 9-julolidinyl, or heteroaromatic substituents are selected from: a reactive substituent R; an unsubstituted, mono-, di-, or tri-substituted phenyl or aryl group; 9-julolidinyl; or an unsubstituted, mono- or di-substituted heteroaromatic group chosen from pyridyl, furanyl, benzofuran-2-yl, benzofuran-3-yl, thienyl, benzothien-2-yl, benzothien-3-yl, dibenzofuranyl, dibenzothienyl, carbazoyl, benzopyridyl, indolinyl, and fluorenyl.

The phenyl, aryl and heteroaromatic substituents (i.e., the substituents of the substituted phenyl, aryl and heteroaromatic groups) of the B and B' groups can each be independently selected from: hydroxyl, a group —C(=O)$R_{21}$, wherein $R_{21}$ is —O$R_{22}$, —N($R_{23}$)$R_{24}$, piperidino, or morpholino, wherein $R_{22}$ is allyl, $C_1$-$C_{20}$ alkyl, phenyl, mono ($C_1$-$C_{20}$)alkyl substituted phenyl, mono($C_1$-$C_{20}$)alkoxy substituted phenyl, phenyl($C_1$-$C_{20}$)alkyl, mono($C_1$-$C_{20}$)alkyl substituted phenyl($C_1$-$C_{20}$)alkyl, mono($C_1$-$C_{20}$)alkoxy substituted phenyl($C_1$-$C_{20}$)alkyl, $C_1$-$C_{20}$ alkoxy($C_2$-$C_{20}$)alkyl or $C_1$-$C_{20}$ haloalkyl, $R_{23}$ and $R_{24}$ are each independently $C_1$-$C_{20}$ alkyl, $C_5$-$C_{10}$ cycloalkyl, phenyl or substituted phenyl, the phenyl substituents being $C_1$-$C_{20}$ alkyl or $C_1$-$C_{20}$ alkoxy, and said halo substituent is chloro or fluoro, aryl, mono($C_1$-$C_{20}$)alkoxyaryl, di($C_1$-$C_{20}$)alkoxyaryl, mono($C_1$-$C_{20}$)alkylaryl, di($C_1$-$C_{20}$)alkylaryl, haloaryl, $C_1$-$C_{10}$ cycloalkylaryl, $C_3$-$C_{10}$ cycloalkyl, $C_3$-$C_{10}$ cycloalkyloxy, $C_3$-$C_{10}$ cycloalkyloxy($C_1$-$C_{20}$)alkyl, $C_3$-$C_{10}$ cycloalkyloxy ($C_1$-$C_{20}$)alkoxy, aryl($C_1$-$C_{20}$)alkyl, aryl($C_1$-$C_{20}$)alkoxy, aryloxy, aryloxy($C_1$-$C_{20}$)alkyl, aryloxy($C_1$-$C_{20}$)alkoxy, mono- or di($C_1$-$C_{20}$)alkylaryl($C_1$-$C_{20}$)alkyl, mono- or di-($C_1$-$C_{20}$) alkoxyaryl($C_1$-$C_{20}$)alkyl, mono- or di-($C_1$-$C_{20}$)alkylaryl($C_1$-$C_{20}$)alkoxy, mono- or di-($C_1$-$C_{20}$)alkoxyaryl($C_1$-$C_{20}$) alkoxy, amino, mono- or di-($C_1$-$C_{20}$)alkylamino, diarylamino, piperazino, N—($C_1$-$C_{20}$)alkylpiperazino, N-arylpiperazino, aziridino, indolino, piperidino, morpholino, thiomorpholino, tetrahydroquinolino, tetrahydroisoquinolino, pyrrolidyl, $C_1$-$C_{20}$ alkyl, $C_1$-$C_{20}$ haloalkyl, $C_1$-$C_{20}$ alkoxy, mono($C_1$-$C_{20}$)alkoxy($C_1$-$C_{20}$)alkyl, acryloxy, methacryloxy, or halogen.

The B and B' groups can also each independently be an unsubstituted or mono-substituted group chosen from pyrazolyl, imidazolyl, pyrazolinyl, imidazolinyl, pyrrolinyl, phenothiazinyl, phenoxazinyl, phenazinyl, and acridinyl, each of said substituents being $C_1$-$C_{20}$ alkyl (e.g., $C_1$-$C_{12}$ alkyl), $C_1$-$C_{20}$ alkoxy (e.g., $C_1$-$C_{12}$ alkoxy), phenyl, or halogen.

In addition, the B and B' groups can each be independently selected from a group represented by the following general Formulas XIVA or XIVB,

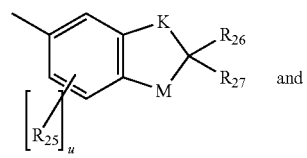

XIVA

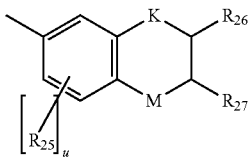

XIVB

Independently with each of general formulas XIVA and XIVB, K is —CH$_2$— or —O—, and M is —O— or substituted nitrogen, provided that when M is substituted nitrogen, K is —CH$_2$—, the substituted nitrogen substituents being hydrogen, $C_1$-$C_{20}$ alkyl, or $C_1$-$C_{20}$ acyl, each $R_{25}$ being independently chosen for each occurrence from $C_1$-$C_{20}$ alkyl, $C_1$-$C_{20}$ alkoxy, hydroxyl, and halogen, $R_{26}$ and $R_{27}$ each being independently hydrogen or $C_1$-$C_{20}$ alkyl, and u is an integer ranging from 0 to 2.

Each B and B' group can independently be a group represented by the following general Formula XXVIII,

XXVIII

With the group represented by general Formula XXVIII, $R_{28}$ is hydrogen or $C_1$-$C_{12}$ alkyl, and $R_{29}$ is an unsubstituted, mono- or di-substituted group chosen from naphthyl, phenyl, furanyl, and thienyl. The substitutents of the mono- or di-substituted naphthyls, phenyls, furanyls, and thienyls, are in each case independently selected from $C_1$-$C_{12}$ alkyl, $C_1$-$C_{12}$ alkoxy, or halogen.

The B and B' groups can together form a member selected from, a fluoren-9-ylidene, a mono-substituted fluoren-9-ylidene, or a di-substituted fluoren-9-ylidene. The substituents of the mono-substituted fluoren-9-ylidene, and the di-substituted fluoren-9-ylidene can in each case be independently selected from $C_1$-$C_{20}$ alkyl (e.g., $C_1$-$C_{12}$ alkyl), $C_1$-$C_{20}$ alkoxy (e.g., $C_1$-$C_{12}$ alkoxy), or halogen.

With some embodiments of the present invention, with the A and B ring fused indenopyran compound, for example, represented by Formulas XV and Xva: $R^1$ for each m, and $R^2$ for each n, are in each case independently selected from $C_1$-$C_6$ alkyl, $C_3$-$C_7$ cycloalkyl, $C_1$-$C_6$ haloalkyl, fluoro, chloro, and —O—$R_{10}$'; $R^3$ and $R^4$ are each independently selected from hydrogen, $C_1$-$C_8$ alkyl, $C_1$-$C_6$ haloalkyl, and $C_3$-$C_7$ cycloalkyl; and B and B' are each independently selected from aryl (e.g., phenyl) substituted with $C_1$-$C_6$ alkoxy, and aryl (e.g., phenyl) substituted with morpholino.

With some embodiments of the present invention, B and B' can each be independently selected from polyalkoxy, and polyalkoxy having a polymerizable group. The polyalkoxy, and polyalkoxy having a polymerizable group from which B and B' can each be independently selected can be represented by the following Formulas XXVI and XXVII.

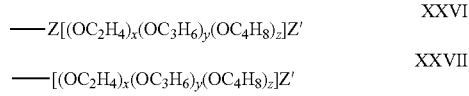

XXVI

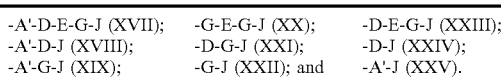

XXVII

With Formulas XXVI and XXVII, —Z is chosen from —C(O)— or —CH$_2$—, Z' is chosen from $C_1$-$C_3$ alkoxy or a polymerizable group. As used herein and in the claims, the term "polymerizable group" means any functional group capable of participating in a polymerization reaction.

With some embodiments, polymerization of the polymerizable indeno-fused ring pyran compounds, such as polymerizable indeno-fused naphthopyrans, can occur by mechanisms described with regard to the definition of "polymerization" in Hawley's Condensed Chemical Dictionary, Thirteenth Edition, 1997, John Wiley & Sons, pages 901-902. Those mechanisms include: by "addition," in which free radicals are the initiating agents that react with the ethylenically unsaturated double bond of the monomer by adding to it on one side at the same time producing a new free electron on the other side; by "condensation," involving the splitting out of a component, such as water molecules, by two reacting monomers; and by so-called "oxidative coupling."

Examples of polymerizable groups include, but are not limited to, hydroxy, thiol, isocyanate groups, oxirane groups (e.g., oxiranylmethyl), radically polymerizable ethylenically unsaturated groups, allyl groups, (meth)acryloxy, and 2-(methacryloxy)ethylcarbamyl. When there are 2 or more polymerizable groups on the indeno-fused ring pyran compound, they can be the same or different.

With some embodiments and with further reference to Formulas XXVI and XXVII: the group, —(OC$_2$H$_4$)$_x$—, can represent poly(ethylene oxide); the group —(OC$_3$H$_6$)$_y$—, can represent poly(propylene oxide); and the group —(OC$_4$H$_8$)$_z$—, can represent poly(butylene oxide). When used in combination, the poly(ethylene oxide), poly(propylene oxide) and poly(butylene oxide) groups of Formulas XXVI and XXVII can be in a random or block order within the polyalkoxy moiety. The subscript letters x, y and z of Formulas XXVI and XXVII are each independently a number between 0 and 50, and the sum of x, y and z is between 2 and 50. The sum of x, y and z can be any number that falls within the range of 2 to 50 (e.g., 2, 3, 4 . . . 50). This sum can also range from any lower number to any higher number within the range of 2 to 50 (e.g., 6 to 50, 31 to 50). The numbers for x, y, and z are average values and can be partial numbers (e.g., 9.5).

As previously discussed, some of the groups of the various compounds and Intermediates described herein, such as each of the $R^1$, $R^2$, $R^3$, $R^4$, B and B' groups, can independently be selected from or include at least one of a reactive substituent and/or a compatiblizing substituent. If the various compounds and/or intermediates described previously herein, such as the indeno-fused ring compound represented by Formula I, the unsaturated compound represented by Formula II, and/or the indeno-fused ring pyran compound represented by Formula XV, include multiple reactive substituents and/or multiple compatiblizing substituents, each reactive substituent and each compatiblizing substituent can be independently chosen.

The reactive substituent and the compatibilizing substituent can each independently be represented in each case by one of:

| | | |
|---|---|---|
| -A'-D-E-G-J (XVII); | -G-E-G-J (XX); | -D-E-G-J (XXIII); |
| -A'-D-J (XVIII); | -D-G-J (XXI); | -D-J (XXIV); |
| -A'-G-J (XIX); | -G-J (XXII); and | -A'-J (XXV). |

With formulas (XVII) through (XXV), non-limiting examples of groups that -A'- can represent according to various non-limiting embodiments disclosed herein include —O—, —C(=O)—, —CH$_2$—, —OC(=O)— and —NHC(=O)—, provided that if -A'-represents —O—, -A'- forms at least one bond with -J.

Non-limiting examples of groups that -D- can represent according to various non-limiting embodiments include a diamine residue, wherein a first amino nitrogen of said diamine residue can form a bond with -A'-, or a substituent or an available position on the compound (such as the indeno-fused naphthol or indeno-fused naphthopyran), and a second amino nitrogen of said diamine residue can form a bond with -E-, -G- or -J; and an amino alcohol residue, wherein an amino nitrogen of the amino alcohol residue can form a bond with -A'-, or a substituent or an available position on the compound (such as the indeno-fused naphthol or indeno-fused naphthopyran), and an alcohol oxygen of said amino alcohol residue can form a bond with -E-, -G- or -J. Alternatively, according to various non-limiting embodiments disclosed herein the amino nitrogen of said amino alcohol residue can form a bond with -E-, -G- or -J, and said alcohol oxygen of said amino alcohol residue can form a bond with -A'-, or a substituent or an available position on the compound (such as the A and B ring fused inden-6-ol compound or A and B ring fused indenopyran compound).

Non-limiting examples of suitable diamine residues that -D- can represent include an aliphatic diamine residue, a cyclo aliphatic diamine residue, a diazacycloalkane residue, an azacyclo aliphatic amine residue, a diazacrown ether residue, and an aromatic diamine residue. Specific non-limiting examples diamine residues that can be used in conjunction with various non-limiting embodiments disclosed herein include the following:

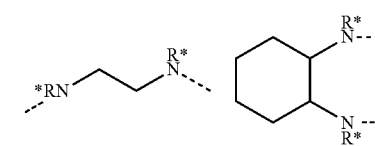
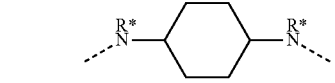
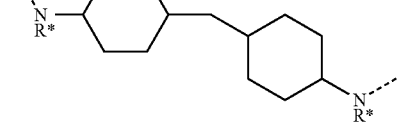
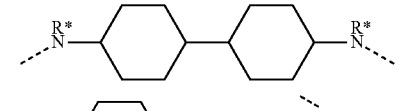
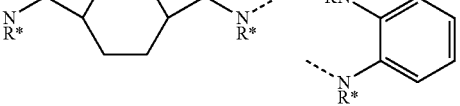
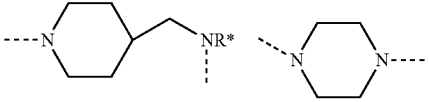

R* = H or alkyl

Non-limiting examples of suitable amino alcohol residues that -D- can represent include an aliphatic amino alcohol residue, a cyclo aliphatic amino alcohol residue, an azacyclo aliphatic alcohol residue, a diazacyclo aliphatic alcohol residue and an aromatic amino alcohol residue. Specific non-limiting examples amino alcohol residues that can be used in conjunction with various non-limiting embodiments disclosed herein include the following:

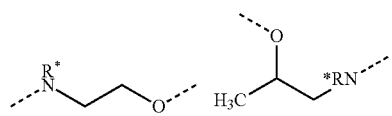

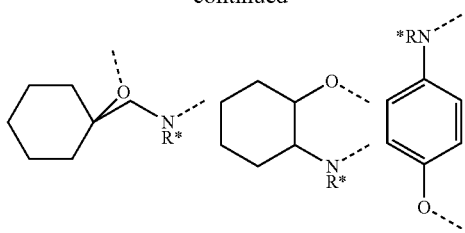
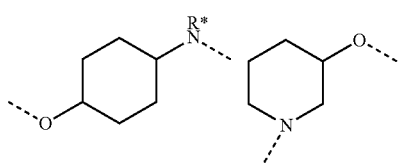
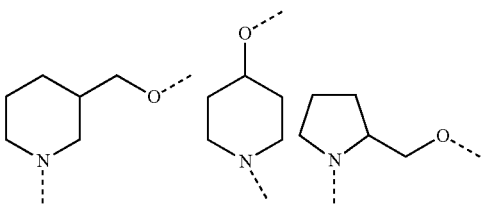
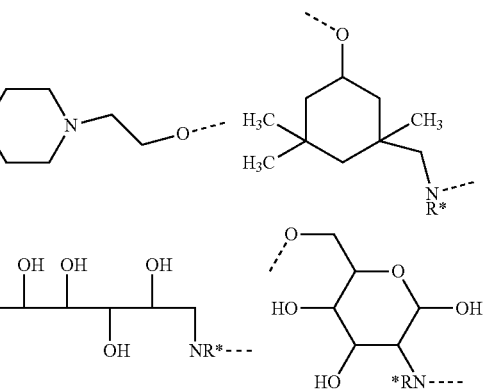

R* = H, alkyl

With continued reference to formulas (XVII) through (XXV) above, according to various non-limiting embodiments disclosed herein, -E- can represent a dicarboxylic acid residue, wherein a first carbonyl group of said dicarboxylic acid residue can form a bond with -G- or -D-, and a second carbonyl group of said dicarboxylic acid residue can form a bond with -G-. Non-limiting examples of suitable dicarboxylic acid residues that -E- can represent include an aliphatic dicarboxylic acid residue, a cycloaliphatic dicarboxylic acid residue and an aromatic dicarboxylic acid residue. Specific non-limiting examples of dicarboxylic acid residues that can be used in conjunction with various non-limiting embodiments disclosed herein include the following:

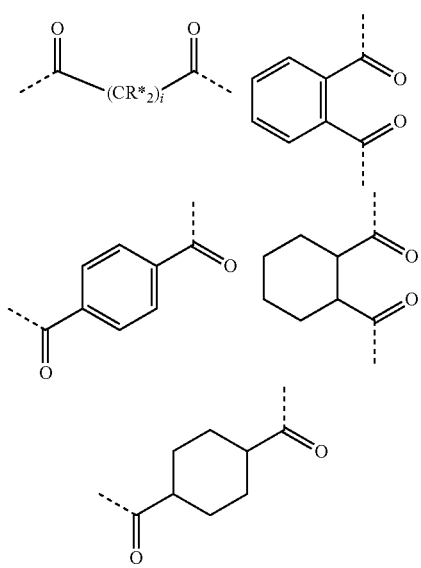

i = 1 to 4
R* = H or alkyl

According to various non-limiting embodiments disclosed herein, -G- can represent a group —[(OC$_2$H$_4$)$_x$(OC$_3$H$_6$)$_y$(OC$_4$H$_8$)$_z$]—O—, wherein x, y and z are each independently chosen and range from 0 to 50, and a sum of x, y, and z ranges from 1 to 50; a polyol residue, wherein a first polyol oxygen of said polyol residue can form a bond with -A'-, -D-, -E-, or a substituent or an available position on the indeno-fused naphthopyran, and a second polyol oxygen of said polyol can form a bond with -E- or -J; or a combination thereof, wherein the first polyol oxygen of the polyol residue forms a bond with a group —[(OC$_2$H$_4$)$_x$(OC$_3$H$_6$)$_y$(OC$_4$H$_8$)$_z$]— (i.e., to form the group —[(OC$_2$H$_4$)$_x$(OC$_3$H$_6$)$_y$ (OC$_4$H$_8$)$_z$]—O—), and the second polyol oxygen forms a bond with -E- or -J. Non-limiting examples of suitable polyol residues that -G- can represent include an aliphatic polyol residue, a cyclo aliphatic polyol residue and an aromatic polyol residue.

More particularly, illustrative and non-limiting examples of polyols from which the polyol residues that -G- can represent can be formed according to various non-limiting embodiments disclosed herein include: (a) low molecular weight polyols having an average molecular weight less than 500, such as, but not limited to, those set forth in U.S. Pat. No. 6,555,028 at col. 4, lines 48-50, and col. 4, line 55 to col. 6, line 5, which disclosure is hereby specifically incorporated by reference herein; (b) polyester polyols, such as, but not limited to, those set forth in U.S. Pat. No. 6,555,028 at col. 5, lines 7-33, which disclosure is hereby specifically incorporated by reference herein; (c) polyether polyols, such as but not limited to those set forth in U.S. Pat. No. 6,555,028 at col. 5, lines 34-50, which disclosure is hereby specifically incorporated by reference herein; (d) amide-containing polyols, such as, but not limited to, those set forth in U.S. Pat. No. 6,555,028 at col. 5, lines 51-62, which disclosure is hereby specifically incorporated by reference; (e) epoxy polyols, such as, but not limited to, those set forth in U.S. Pat. No. 6,555,028 at col. 5 line 63 to col. 6, line 3, which disclosure is hereby specifically incorporated by reference herein; (f) polyhydric polyvinyl alcohols, such as, but not limited to, those set forth in U.S. Pat. No. 6,555,028 at col. 6, lines 4-12, which disclosure is hereby specifically incorporated by reference herein; (g) urethane polyols, such as, but not limited to those set forth in U.S. Pat. No. 6,555,028 at col. 6, lines 13-43, which disclosure is hereby specifically incorporated by reference herein; (h) polyacrylic polyols, such as, but not limited to those set forth in U.S. Pat. No. 6,555,028 at col. 6, lines 43 to col. 7, line 40, which disclosure is hereby specifically incorporated by reference herein; (i) polycarbonate polyols, such as, but not limited to, those set forth in U.S. Pat. No. 6,555,028 at col. 7, lines 41-55, which disclosure is hereby specifically incorporated by reference herein; and (j) mixtures of such polyols.

With further reference to formulas (XVII) through (XXV), according to various non-limiting embodiments disclosed herein, -J can represent a group —K, wherein —K represents a group such as, but not limited to, —CH$_2$COOH, —CH(CH$_3$)COOH, —C(O)(CH$_2$)$_w$COOH, —C$_6$H$_4$SO$_3$H, —C$_5$H$_{10}$SO$_3$H, —C$_4$H$_8$SO$_3$H, —C$_3$H$_6$SO$_3$H, —C$_2$H$_4$SO$_3$H and —SO$_3$H, wherein "w" ranges from 1 to 18. According to other non-limiting embodiments -J can represent hydrogen that forms a bond with an oxygen or a nitrogen of linking group to form a reactive moiety such as —OH or —NH. For example, according to various non-limiting embodiments disclosed herein, -J can represent hydrogen, provided that if -J represents hydrogen, -J is bonded to an oxygen of -D- or -G-, or a nitrogen of -D-.

According to still further non-limiting embodiments, -J can represent a group -L or residue thereof, wherein -L can represent a reactive moiety. For example, according to various non-limiting embodiments disclosed herein -L can represent a group such as, but not limited to, acryl, methacryl, crotyl, 2-(methacryloxy)ethylcarbamyl, 2-(methacryloxy)ethoxycarbonyl, 4-vinylphenyl, vinyl, 1-chlorovinyl or epoxy. As used herein, the terms acryl, methacryl, crotyl, 2-(methacryloxy)ethylcarbamyl, 2-(methacryloxy)ethoxycarbonyl, 4-vinylphenyl, vinyl, 1-chlorovinyl, and epoxy refer to the following structures:

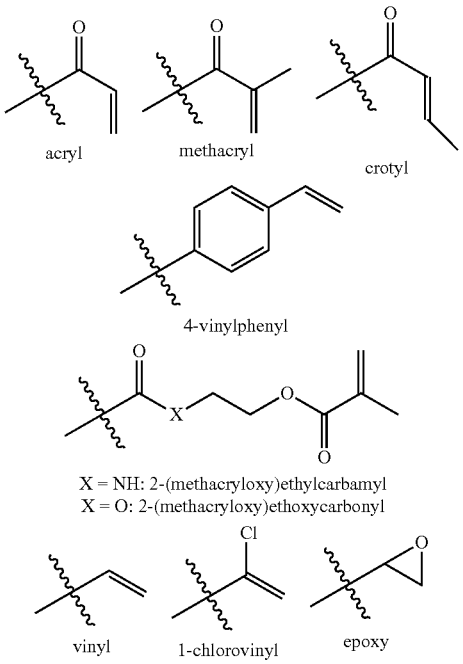

X = NH: 2-(methacryloxy)ethylcarbamyl
X = O: 2-(methacryloxy)ethoxycarbonyl

As previously discussed, -G- can represent a residue of a polyol, which is defined herein to include hydroxy-containing carbohydrates, such as those set forth in U.S. Pat. No. 6,555,028 at col. 7, line 56 to col. 8, line 17, which disclosure is hereby specifically incorporated by reference herein. The polyol residue can be formed, for example and without limitation herein, by the reaction of one or more of the polyol hydroxyl groups with a precursor of -A'-, such as a carboxylic acid or a methylene halide, a precursor of polyalkoxylated group, such as polyalkylene glycol, or a hydroxyl substituent of the A and B ring fused indenopyran compound. The polyol can be represented by $q\text{-}(OH)_a$ and the residue of the polyol can be represented by the formula $-O\text{-}q\text{-}(OH)_{a-1}$, wherein q is the backbone or main chain of the polyhydroxy compound and "a" is at least 2.

Further, as discussed above, one or more of the polyol oxygens of -G- can form a bond with -J (i.e., forming the group -G-J). For example, although not limiting herein, wherein the reactive and/or compatiblizing substituent comprises the group -G-J, if -G- represents a polyol residue and -J represents a group —K that contains a carboxyl terminating group, -G-J can be produced by reacting one or more polyol hydroxyl groups to form the group —K (for example as discussed with respect to Reactions B and C at col. 13, line 22 to col. 16, line 15 of U.S. Pat. No. 6,555,028, which disclosure is hereby specifically incorporated by reference herein) to produce a carboxylated polyol residue. Alternatively, if -J represents a group —K that contains a sulfo or sulfono terminating group, although not limiting herein, -G-J can be produced by acidic condensation of one or more of the polyol hydroxyl groups with $HOC_6H_4SO_3H$; $HOC_5H_{10}SO_3H$; $HOC_4H_8SO_3H$; $HOC_3H_6SO_3H$; $HOC_2H_4SO_3H$; or $H_2SO_4$, respectively. Further, although not limiting herein, if -G- represents a polyol residue and -J represents a group -L chosen from acryl, methacryl, 2-(methacryloxy)ethylcarbamyl and epoxy, -L can be added by condensation of the polyol residue with acryloyl chloride, methacryloyl chloride, 2-isocyanatoethyl methacrylate or epichlorohydrin, respectively.

The A and B ring fused indenopyran compounds prepared by the methods of the present invention, can be used to render compositions and/or articles photochromic. Examples of articles that can be rendered photochromic by the indeno-fused ring pyran compounds of the present invention include, but are not limited to, optical elements, displays, windows (or transparencies), mirrors, and components or elements of liquid crystal cells. As used herein the term "optical" means pertaining to or associated with light and/or vision. Examples of optical elements that can be rendered photochromic include, without limitation, ophthalmic elements, display elements, windows, mirrors, and liquid crystal cell elements. As used herein the term "ophthalmic" means pertaining to or associated with the eye and vision. Non-limiting examples of ophthalmic elements include corrective and non-corrective lenses, including single vision or multi-vision lenses, which can be either segmented or non-segmented multi-vision lenses (such as, but not limited to, bifocal lenses, trifocal lenses and progressive lenses), as well as other elements used to correct, protect, or enhance (cosmetically or otherwise) vision, including without limitation, magnifying lenses, protective lenses, visors, goggles, as well as, lenses for optical instruments (for example, cameras and telescopes). As used herein the term "display" means the visible or machine-readable representation of information in words, numbers, symbols, designs or drawings. Non-limiting examples of display elements include screens, monitors, and security elements, such as security marks. As used herein the term "window" means an aperture adapted to permit the transmission of radiation there-through. Non-limiting examples of windows include automotive and aircraft transparencies, windshields, filters, shutters, and optical switches. As used herein the term "mirror" means a surface that specularly reflects a large fraction of incident light. As used herein the term "liquid crystal cell" refers to a structure containing a liquid crystal material that is capable of being ordered. One non-limiting example of a liquid crystal cell element is a liquid crystal display.

Articles can be rendered photochromic with the indeno-fused ring pyran compounds of the present invention by methods including, but not limited to, imbibition methods, cast-in-place methods, coating methods, in-mold coating methods, over-mold methods, and lamination methods. With imbibition methods, the indeno-fused ring pyran compound is typically diffused into a polymeric material of a previously formed or fabricated article, such as a substrate or previously applied coating or film. Imbibition can be performed by immersing the polymeric material of a previously formed or fabricated article in a solution containing the A and B ring fused indenopyran compound, with or without heating. Thereafter, although not required, the A and B ring fused indenopyran compound can be bonded with the polymeric material (e.g., of the substrate or coating).

With cast-in-place methods, the A and B ring fused indenopyran compound can be mixed with: a polymer and/or oligomer composition in solution or melt form; or monomer composition in liquid form, so as to form a castable photochromic composition. The castable photochromic composition is then typically introduced into the cavity of a mold (e.g., a lens mold). The castable photochromic composition is then set (e.g., cured) within the mold so as to form a photochromic article.

With articles that include a substrate, the A and B ring fused indenopyran compounds of the present invention can be connected to at least a portion of the substrate as part of a coating that is connected to at least a portion of the substrate. The substrate can be a polymeric substrate or an inorganic substrate (such as, but not limited to, a glass substrate). The A and B ring fused indenopyran compound of the present invention can be incorporated into at least a portion of a coating composition prior to application of the coating composition to the substrate. Alternatively, a coating composition can be applied to the substrate, at least partially set, and thereafter the A and B ring fused indenopyran compound of the present invention can be imbibed into at least a portion of the coating. As used herein, the terms "set" and "setting" include, without limitation, curing, polymerizing, cross-linking, cooling, and drying.

Photochromic articles can be prepared using the A and B ring fused indenopyran compounds of the present invention by art-recognized in-mold coating (or in-mold casting) methods. With in-mold coating methods, a photochromic coating composition including the A and B ring fused indenopyran compound of the present invention, which can be a liquid coating composition or a powder coating composition, is applied to at least a portion of the interior surface of a mold, and then at least partially set. Thereafter, a polymer solution or melt, or oligomeric or monomeric solution or mixture is cast or molded within the mold cavity and in contact with the previously applied photochromic coating composition, and at least partially set. The resulting photochromic article is then removed from the mold. Non-limiting examples of powder coatings in which the A and B ring fused indenopyran compounds according to various non-limiting embodiments disclosed herein can be employed are set forth in U.S. Pat. No. 6,068,797 at col. 7, line 50 to col. 19, line 42, which disclosure is hereby specifically incorporated by reference herein.

Photochromic articles prepared using the A and B ring fused indenopyran compounds of the present invention can also be formed by art-recognized over-mold methods. Over-mold methods typically involve forming a substrate within a mold, and then forming an interior space between the substrate and an interior surface of the mold, into which a photochromic coating composition is then subsequently introduced (e.g., injected) and then set (e.g., cured). Alternatively, over-mold methods can involve introducing a previously formed substrate into a mold, such that an interior space is defined between the substrate and an interior mold surface, and thereafter a photochromic coating composition is introduced (e.g., injected) into the interior space.

Photochromic articles, prepared using the A and B ring fused indenopyran compounds prepared by the methods of the present invention, can also be formed by art-recognized lamination methods. With lamination methods, a film comprising the A and B ring fused indenopyran compounds of the present invention can be adhered or otherwise connect to a portion of the substrate, with or without an adhesive and/or the application of heat and pressure. Thereafter, if desired, a second substrate can be applied over the first substrate and the two substrates can be laminated together (e.g., by the application of heat and pressure) to form an element wherein the film comprising the A and B ring fused indenopyran compound is interposed between the two substrates. Methods of forming films comprising a photochromic material can include for example and without limitation, combining a photochromic material with a polymeric solution or oligomeric solution or mixture, casting or extruding a film therefrom, and, if required, at least partially setting the film. Additionally or alternatively, a film can be formed (with or without a photochromic material) and imbibed with the photochromic material.

The A and B ring fused indenopyran compounds prepared by the methods of the present invention, can be used alone or in combination with other photochromic materials. Classes of photochromic materials that can be used in combination (e.g., in mixture) with the A and B ring fused indenopyran compounds of the present invention include, but are not limited to: spiro(indoline)naphthoxazines and spiro(indoline)benzoxazines, for example as described in U.S. Pat. Nos. 3,562,172, 3,578,602, 4,215,010, 4,342,668, 5,405,958, 4,637,698, 4,931,219, 4,816,584, 4,880,667, and 4,818,096; benzopyrans, for example as described in U.S. Pat. Nos. 3,567,605, 4,826,977, 5,066,818, 4,826,977, 5,066,818, 5,466,398, 5,384,077, 5,238,931, and 5,274,132; photochromic organo-metal dithizonates, such as, (arylazo)-thioformic arylhydrazidates, e.g., mercury dithizonates which are described in, for example, U.S. Pat. No. 3,361,706; and fulgides and fulgimides, e.g., the 3-furyl and 3-thienyl fulgides and fulgimides which are described in U.S. Pat. No. 4,931,220 at column 20, line 5 through column 21, line 38.

The present invention is more particularly described in the following examples, which are intended to be illustrative only, since numerous modifications and variations therein will be apparent to those skilled in the art. Unless otherwise specified, all parts and all percentages are by weight.

EXAMPLES

In Part 1 of the Examples, the synthesis procedures used to make the naphthols and photochromic materials according to various non-limiting embodiments disclosed herein are set forth in Examples 1-4 and IA-4A. Part 2 describes the photochromic performance testing and results for photochromic compounds of Examples 2A-4A.

Example 1

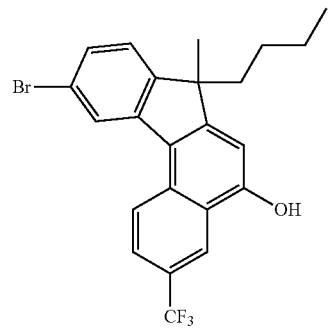 [SMILES: CCCCC1(C)c2ccc(Br)cc2-c2c1cc(O)c1cc(C(F)(F)F)ccc21]

Step 1

A mixture of 4-bromoacetophenone (148 g), dimethyl succinic ester (130 g) and toluene (2.5 L) was mechanically stirred in a reaction flask. Potassium t-butoxide (100 g) was added in one portion. A yellow color was observed and a lot of precipitate formed. One hour later, water (1 L) was added. The water layer was collected and washed with toluene (200 mL) twice. It was then acidified to pH 3 using 12 N HCl and extracted with ethyl acetate (1 L). The ethyl acetate solution was collected, dried over magnesium sulfate and concentrated. To the resulting viscous mixture, hexane (1 L) was added. A large amount of oil precipitated out and then crystallized. After filtration, white crystals (170 g) were obtained as the product. NMR showed that the product had a structure consistent with (E)-4-(4-bromophenyl)-3-(methoxycarbonyl)pent-3-enoic acid.

Step 2

The product of Step 1 (160 g) was mixed with 50% sodium hydroxide water solution (200 g) and water (4 liters) in a four liter beaker. The mixture was heated to boil. After one hour, the mixture was cooled to room temperature and the pH of the mixture was adjusted to 2 using 12 N HCl. The precipitated off-white crystals were collected by filtration and dried to yield 152 grams of product. NMR showed that the product had a structure consistent with (E)-2-(1-(4-bromophenyl)ethylidene)succinic acid.

Step 3

A mixture of the product of Step 2 (152 g), DBSA (5 g) and toluene (1 L) was heated up to reflux with water removed by a Dean-Stark trap. After 2 hours, the mixture was cooled to room temperature and then passed through a silica gel plug column using 2/8 ethyl acetate/hexanes as the eluent. After concentration, oil was obtained. To the oil, hexanes (1 L) was added and the product crystallized out. It was collected by filtration and dried in vacuum to yield off-white crystals (130 grams) as the product. NMR showed that the product had a structure consistent with (E)-3-(1-(4-bromophenyl)ethylidene)dihydrofuran-2,5-dione.

Step 4

To a stirred mixture of the aluminum chloride (130 g) and methylene chloride (1 L), the product of Step 3 (125 g) was added in three portions in 5 minutes. After stirring at room temperature for 2 hours, the reaction mixture was poured into water (2 L) slowly. THF (1 L) and solid sodium chloride (100 g) was then added to the mixture. The resulting water layer was removed by a separatory funnel. The recovered organic layer was dried over magnesium sulfate and concentrated. Ethyl acetate (200 ml) was added and the resulting yellow crystals were collected and dried to yield 50 grams of product. NMR showed that the product had a structure consistent with 2-(6-bromo-3-methyl-1-oxo-1H-inden-2-yl) acetic acid.

Step 5

A mixture of manganese chloride (7.46 g) and lithium chloride (5 g) was dried at 200° C. in a vacuum oven for an hour. Under the protection of nitrogen, THF was added (200 ml) and the mixture was stirred for 30 minutes until a clear solution was obtained. To the solution, copper (I) chloride (0.59 g) and the product of Step 4 (19.4 g) were added. The mixture was stirred until clear and then cooled to 0° C. To the mixture, 2M THF solution of butyl magnesium bromide (99 ml) was added dropwise. The reaction mixture turned black eventually with the addition of more BuMgBr. The addition was completed in 2 hours. After the addition, the mixture was stirred at 0° C. for 2 hours and then quenched using water (200 mL). The pH of the mixture was adjusted to ~2 using 12 N HCl. Ethyl acetate (200 mL) was added. The resulting organic portion was collected by a separatory funnel, dried, and concentrated. The product was purified by CombiFlash® Rf from Teledyne ISCO to yield oil (4 g) as the product. NMR showed that the product had a structure consistent with 2-(5-bromo-1-butyl-1-methyl-3-oxo-2,3-dihydro-1H-inden-2-yl)acetic acid.

Step 6

Under the protection of nitrogen, solid magnesium (1.1 g) was placed in a dried reaction flask. THF (60 mL) and 1-bromo-4-trifluoromethylbenzene (10.3 g) was added. The mixture was stirred at room temperature. Ice bath was used occasionally to control the reaction temperature to about room temperature. After two hours the resulting Grignard solution was transferred to a dropping funnel that was attached to another dried reaction flask, in which a mixture of anhydrous THF (300 ml), anhydrous lanthanum chloride (11.3 g) and anhydrous lithium chloride (5.8 g) was stirred until clear. The product of Step 5 (3.9 g) was added to the flask. The resulting mixture was stirred for 10 minutes at room temperature and then cooled in an ice bath. The Grignard in the dropping funnel was added into the stirred reaction mixture over 10 minutes and the mixture was stirred at room temperature for 4 hours.

The reaction was stopped by the addition of water (100 mL). The pH was adjusted to 2 using 12 N HCl. Ethyl acetate was added (100 mL). The resulting organic phase was collected by a separatory funnel, washed with NaCl/water, dried over magnesium sulfate and concentrated.

The recovered oil was re-dissolved in toluene (100 mL) in a reaction flask. Acetic anhydride (10 grams) and bismuth triflate (0.04 g) were added. The mixture was refluxed for 2 hours and cooled to room temperature. Methanol (100 mL) and 12 N HCl (1 mL) were added. The mixture was refluxed for 12 hours and then concentrated. The crude product was purified by silica gel plug column separation using 2/8 ethyl acetate/hexane as the eluent. Oil (3 g) was obtained as the product. NMR showed that the product had a structure consistent with 10-bromo-7-butyl-7-methyl-3-(trifluoromethyl)-7H-benzo[c]fluoren-5-ol.

Example 1A

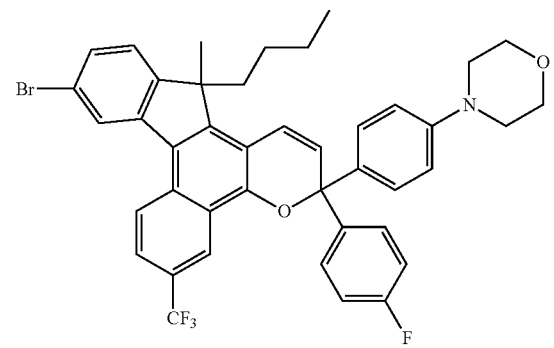 [SMILES: CCCCC1(C)c2ccc(Br)cc2-c2c1c1c(c3cc(C(F)(F)F)ccc23)OC(c2ccc(F)cc2)(c2ccc(N3CCOCC3)cc2)C=C1]

The product of Example 1 (3 g) was placed in a reaction flask. To the flask, 1-(4-fluorophenyl)-1-(4-(N-morpholino)phenyl)prop-2-yn-1-ol (2.1 g), 1,2-dichloroethane (30 ml) and p-toluenesulfonic acid (70 mg) was added. The mixture was refluxed for 4 hours, concentrated and passed through a silica gel plug column using 2/8 ethyl acetate/hexane as the solvent. A brownish oil (2 grams) was obtained as the product. NMR showed that the product had a structure consistent with 3-(4-fluorophenyl)-3-(4-(N-morpholino)phenyl)-10-bromo-6-trifluoromethyl-13-methyl-13-butyl-3H,13H-indeno[2',3':3,4]naphtho[1,2-b]pyran.

Example 2

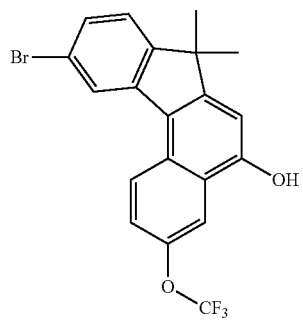 [SMILES: CC1(C)c2ccc(Br)cc2-c2c1cc(O)c1cc(OC(F)(F)F)ccc21]

The procedures from Example 1 were followed except that: in Step 5, 1.4 M THF solution of methyl magnesium bromide was used in place of butyl magnesium bromide; in Step 6, 1-bromo-4-trifluoromethoxybenzene was used in place of 1-bromo-4-trifluoromethylbenzene. NMR showed that the product had a structure consistent with 10-bromo-7,7-dimethyl-3-(trifluoromethoxy)-7H-benzo[c]fluoren-5-ol.

Example 2A

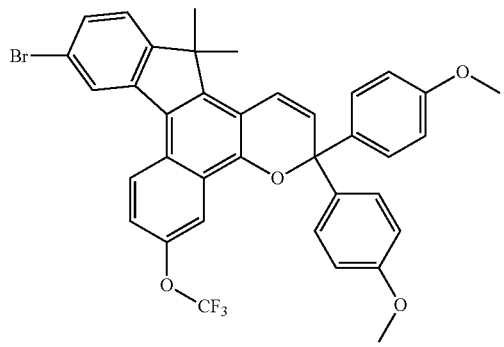 [SMILES: COc1ccc(C2(c3ccc(OC)cc3)C=Cc3c4c(c5ccc(OC(F)(F)F)cc5c3O2)-c2cc(Br)ccc2C4(C)C)cc1]

The procedures from Example 1A were followed except that the product of Example 2 was used in place of the product of Example 1 and 1,1-bis(4-methoxyphenyl)prop-2-yn-1-ol was used in place of 1-(4-fluorophenyl)-1-(4-(N-morpholino)phenyl)prop-2-yn-1-ol. NMR showed that the product had a structure consistent with 3,3-bis(4-methoxyphenyl)-10-bromo-6-trifluoromethoxy-13,13-dimethyl-3H,13H-indeno[2',3':3,4]naphtho[1,2-b]pyran.

Example 3

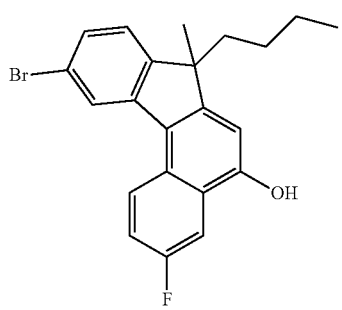 [SMILES: CCCCC1(C)c2ccc(Br)cc2-c2c1cc(O)c1cc(F)ccc21]

The procedures from Example 1 were followed except that in Step 6, 1-bromo-4-fluorobenzene was used in place of 1-bromo-4-trifluoromethylbenzene. NMR showed that the product had a structure consistent with 10-bromo-7-butyl-3-fluoro-7-methyl-7H-benzo[c]fluoren-5-ol.

Example 3A

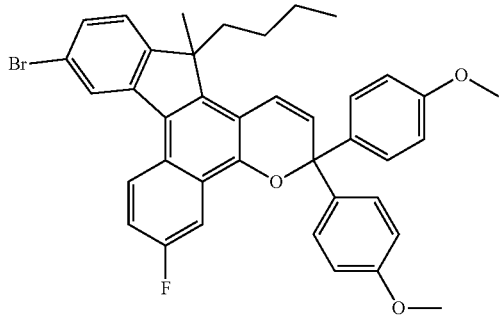 [SMILES: CCCCC1(C)c2ccc(Br)cc2-c2c1c1c(c3cc(F)ccc23)OC(c2ccc(OC)cc2)(c2ccc(OC)cc2)C=C1]

The procedures from Example 1A were followed except that the product of Example 3 was used in place of the product of Example 1 and 1,1-bis(4-methoxyphenyl)prop-2-yn-1-ol was used in place of 1-(4-fluorophenyl)-1-(4-(N-morpholino)phenyl)prop-2-yn-1-ol. NMR showed that the product had a structure consistent with 3,3-bis(4-methoxyphenyl)-10-bromo-6-fluoro-13-methyl-13-butyl-3H,13H-indeno[2',3':3,4]naphtho[1,2-b]pyran.

Example 4

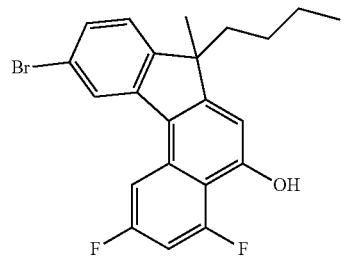 [SMILES: CCCCC1(C)c2ccc(Br)cc2-c2c1cc(O)c1c(F)cc(F)cc21]

The procedures from Example 1 were followed except that in Step 6, 1-bromo-3,5-difluorobenzene was used in place of 1-bromo-4-trifluoromethylbenzene. NMR showed that the product had a structure consistent with 10-bromo-7-butyl-2,4-difluoro-7-methyl-7H-benzo[c]fluoren-5-ol.

Example 4A

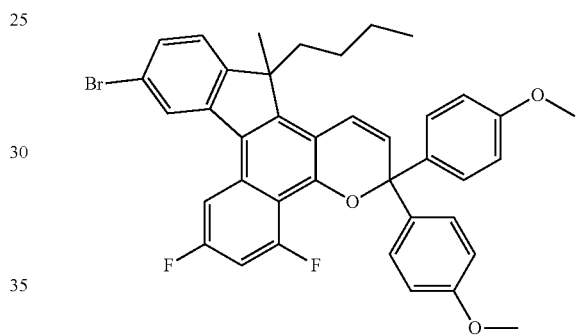

The procedures from Example 1A were followed except that the product of Example 4 was used in place of the product of Example 1 and 1,1-bis(4-methoxyphenyl)prop-2-yn-1-ol was used in place of 1-(4-fluorophenyl)-1-(4-(N-morpholino)phenyl)prop-2-yn-1-ol. NMR showed that the product had a structure consistent with 3,3-bis(4-methoxyphenyl)-10-bromo-5,7-fluoro-13-methyl-13-butyl-3H, 13H-indeno[2',3':3,4]naphtho[1,2-b]pyran.

Part 2: Photochromic Performance Testing and Results

The photochromic performance of the photochromic materials of Examples 2A-4A were tested as follows. A quantity of the photochromic material to be tested, calculated to yield a $1.5 \times 10^{-3}$ M solution, was added to a flask containing 50 grams of a monomer blend of 4 parts ethoxylated bisphenol A dimethacrylate (BPA 2EO DMA), 1 part poly(ethylene glycol) 600 dimethacrylate, and 0.033 weight percent 2,2'-azobis(2-methyl propionitrile) (AIBN). The photochromic material was dissolved into the monomer blend by stirring and gentle heating if necessary. After a clear solution was obtained, it was vacuum degassed before being poured into a flat sheet mold having the interior dimensions of 2.2 mm×6 inches (15.24 cm)×6 inches (15.24 cm). The mold was sealed and placed in a horizontal air flow, programmable oven programmed to increase the temperature from 40° C. to 95° C. over a 5 hour interval, hold the temperature at 95° C. for 3 hours and then lower it to 60° C. for over a 2 hour interval. After the mold was opened, the polymer sheet was cut using a utility knife to score the surface and snap into 2 inch (5.1 cm) test squares.

The photochromic test squares prepared as described above were tested for photochromic response on an optical bench. Prior to testing on the optical bench, the photochromic test squares were exposed to 365 nm ultraviolet light for about 15 minutes to cause the photochromic material to transform from the ground state-form to an activated-state form, and then placed in a 75° C. oven for about 15 minutes to allow the photochromic material to revert back to the ground state-form. The test squares were then cooled to room temperature, exposed to fluorescent room lighting for at least 2 hours, and then kept covered (that is, in a dark environment) for at least 2 hours prior to testing on an optical bench maintained at 73° F. (23° C.).

The optical bench fitted with a Schott 3 mm KG-2 band-pass filter, neutral density filter(s) and a Newport Model#67005 300-watt Xenon arc lamp with Model#69911 power supply in association with a Newport Model 689456 Digital Exposure/Timer was used to control the intensity of the irradiance beam utilized for activation of the sample. A Uniblitz model# CS25S3ZM0 with model# VMM-D3 controller) high-speed computer controlled shutter, a fused silica condensing lens for beam collimation of this activation lamp beam though a quartz glass water bath sample chamber.

A custom made broadband light source for monitoring response measurements was directed through the sample such that the angle between the activation source and the monitoring beam is 30 degrees with the sample positioned perpendicular to this monitoring beam. This broad beam light source is obtained by collecting and combining separately filtered light from a 100-Watt tungsten halogen lamp (controlled by a Lambda UP60-14 constant voltage powder supply) with a split-end, bifurcated fiber optical cable to enhance the short wavelength light intensity. After passing through the sample, this monitoring light was refocused into a 2-inch integrating sphere and fed to an Ocean Optics S2000 spectrophotometer by fiber optic cables. Ocean Optics SpectraSuite and PPG proprietary software were used to measure response and control the operation of the optical bench.

The $\lambda_{max-vis}$ is the wavelength in the visible spectrum at which the maximum absorption of the activated-state form of the photochromic compound in a test square occurs. The $\lambda_{max-vis}$ wavelength was determined by testing the photochromic test squares in a Varian Cary 4000 UV-Visible spectrophotometer; it may also be calculated from the spectrum obtained by the S2000 spectrometer on the optical bench.

The change in Optical density at saturation for each test sample was determined by opening the shutter from the xenon lamp and measuring the transmittance after exposing the test chip to 3 W/m2 UVA radiation for 30 minutes. The change in Optical density at saturation was calculated using the formula: $\Delta OD=\log$ (% Tb/% Ta), where % Tb is the percent transmittance in the bleached state, % Ta is the percent transmittance in the activated state both at the $\lambda_{max-vis}$ and the logarithm is to the base 10. The first fade half life ("$T_{1/2}$") or bleach rate is the time interval in seconds for the absorbance of the activated-state form of the photochromic material in the test squares to reach one half the $\Delta OD$ at saturation value at room temperature (23° C.), after removal of the source of activating light. The Sensitivity ($\Delta OD$/Min) is a measure of how quickly the sample darkens and is calculated from the equation $\Delta OD_{sen}=\Delta OD_{5min}\times 12$.

TABLE 1

Photochromic Performance Test Results

| Example # (Compound #) | $\lambda_{max\text{-}vis}$ (nm) | Sensitivity ($\Delta$OD/Min) | $\Delta$OD at saturation | T ½ (sec) |
|---|---|---|---|---|
| 2A | 572 | 0.44 | 0.27 | 35 |
| 3A | 564 | 0.46 | 0.34 | 44 |
| 4A | 551 | 0.65 | 0.44 | 35 |

The present invention has been described with reference to specific details of particular embodiments thereof. It is not intended that such details be regarded as limitations upon the scope of the invention except insofar as and to the extent that they are included in the accompanying claims.

We claim:

1. A method of making an indeno-fused ring pyran compound represented by the following Formula XV,

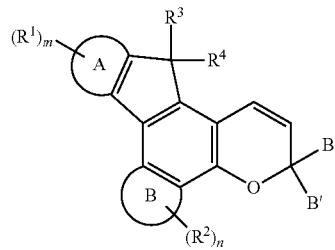

XV wherein Ring-A and Ring-B are each independently selected from unsubstituted aryl, substituted aryl, unsubstituted fused ring aryl, substituted fused ring aryl, unsubstituted heteroaryl, and substituted heteroaryl, m and n are each independently selected from 0 to 4, $R^1$ for each m, and $R^2$ for each n, are in each case independently selected from hydrocarbyl optionally interrupted with at least one of —O—, —S—, —C(O)—, —C(O)O—, —S(O)—, —SO$_2$—, —N=N—, —N(R$_{11}$')— where R$_{11}$' is selected from hydrogen, hydrocarbyl or substituted hydrocarbyl, —Si(OR$_{13}$')$_k$(R$_{13}$')$_j$—, where k and j are each independently selected from 0 to 2, provided that the sum of k and j is 2, and each R$_{13}$' is independently selected from hydrogen, hydrocarbyl and substituted hydrocarbyl, and combinations of two or more thereof; substituted hydrocarbyl optionally interrupted with at least one of —O—, —S—, —C(O)—, —C(O)O—, —S(O)—, —SO$_2$—, —N=N—, —N(R$_{11}$')— where R$_{11}$' is selected from hydrogen, hydrocarbyl or substituted hydrocarbyl, —Si(OR$_{13}$')$_k$(R$_{13}$')$_j$—, where k and j are each independently selected from 0 to 2, provided that the sum of k and j is 2, and each R$_{13}$' is independently selected from hydrogen, hydrocarbyl and substituted hydrocarbyl, and combinations of two or more thereof; halogen; cyano; —O—R$_{10}$' or —C(O)—R$_{10}$' or —C(O)—OR$_{10}$', wherein each R$_{10}$' is independently selected from hydrogen, hydrocarbyl or substituted hydrocarbyl; and —N(R$_{11}$')R$_{12}$', wherein R$_{11}$' and R$_{12}$' are each independently selected from hydrogen, hydrocarbyl or substituted hydrocarbyl, or R$_{11}$' and R$_{12}$' together form a ring structure optionally including at least one heteroatom, and $R^3$ and $R^4$ are each independently selected from hydrogen; hydrocarbyl optionally interrupted with at least one of —O—, —S—, —C(O)—, —C(O)O—, —S(O)—, —SO$_2$—, —N=N—, and —N(R$_{11}'$)— where R$_{11}'$ is selected from hydrogen, hydrocarbyl or substituted hydrocarbyl, and combinations of two or more thereof; and substituted hydrocarbyl optionally interrupted with at least one of —O—, —S—, —C(O)—, —C(O)O—, —S(O)—, —SO$_2$—, —N=N—, and —N(R$_{11}'$)— where R$_{11}'$ is selected from hydrogen, hydrocarbyl or substituted hydrocarbyl, and combinations of two or more thereof, and B and B' are each independently selected from unsubstituted aryl, substituted aryl, unsubstituted heteroaryl, substituted heteroaryl, polyalkoxy, and polyalkoxy having a polymerizable group, or B and B' taken together form a ring structure selected from unsubstituted fluoren-9-ylidene, substituted fluoren-9-ylidene, saturated spiro-monocyclic hydrocarbon ring, saturated spiro-bicyclic hydrocarbon ring, and spiro-tricyclic hydrocarbon ring, said method comprising, (a) reacting an unsaturated compound represented by Formula II, with at least one of an organo metal hydride and a first nucleophile represented by Formula III, thereby forming a saturated compound represented by Formula IV,

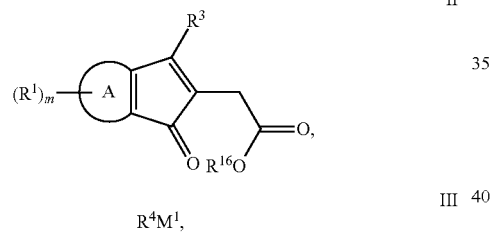

II $R^4 M^1$,

III wherein $R^4$ is a nucleophile of $R^4$ as described with regard to Formula (I), and $M^1$ is selected from Si(R$^{18}$)$_3$, where each R$^{18}$ is independently selected from C$_1$-C$_8$ alkyl, or $M^1$ represents a counterion comprising a metal selected from Mg, Li, Mn, Cu, Zn, and combinations thereof,

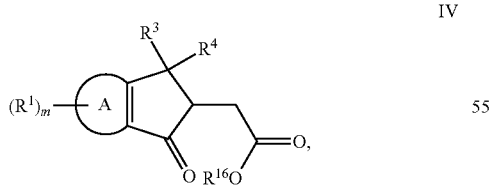

IV $R^{16}$ of Formulas II and IV being selected from hydrogen, hydrocarbyl and substituted hydrocarbyl, (b) reacting the saturated compound represented by Formula IV with a second nucleophile represented by Formula V, thereby forming a substituted intermediate represented by at least one of Formula VI, Formula VII and Formula VIII,

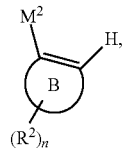

V wherein for the second nucleophile represented by Formula V, Ring-B is a nucleophile of Ring-B as described with regard to Formula (I), and $M^2$ represents a counterion comprising a metal selected from Mg, Li, Mn, Cu, Zn, Ln, and combinations thereof,

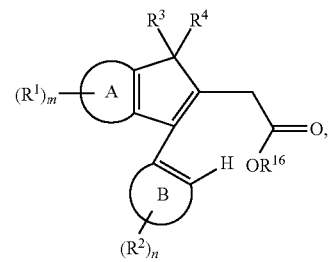

VI

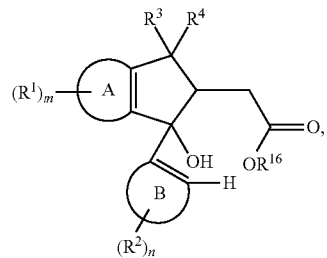

VII

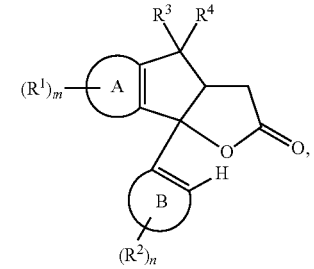

VIII and (c) converting said substituted intermediate represented by at least one of Formula VI, Formula VII and Formula VIII to compound represented by Formula I,

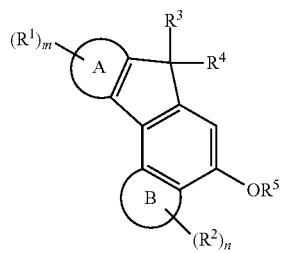

I wherein $R^5$ is selected from hydrogen, —C(O)—$R^{13}$ or —S(O)(O)$R^{13}$ wherein $R^{13}$ is hydrocarbyl, or halohydrocarbyl, and (d) reacting the compound represented by Formula I with a propargyl alcohol represented by Formula XVI, thereby forming said A and B ring fused indenopyran compound represented by Formula XV,

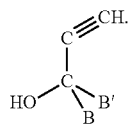

XVI

2. The method of claim 1, wherein,

Ring-A and Ring-B are each independently selected from unsubstituted aryl and substituted aryl;

$R^1$ for each m, and $R^2$ for each n, are in each case independently selected from, halogen selected from fluoro and chloro;
$C_1$-$C_{20}$ alkyl;
$C_3$-$C_{10}$ cycloalkyl;
substituted or unsubstituted phenyl, the phenyl substituents being selected from hydroxyl, halogen, carbonyl, $C_1$-$C_{20}$ alkoxycarbonyl, cyano, halo($C_1$-$C_{20}$) alkyl, $C_1$-$C_{20}$ alkyl or $C_1$-$C_{20}$ alkoxy;
—O—$R_{10}$' or —C(O)—$R_{10}$' or —C(O)—O$R_{10}$', wherein $R_{10}$' is hydrogen, $C_1$-$C_{20}$ alkyl, phenyl($C_1$-$C_{20}$)alkyl, mono($C_1$-$C_{20}$)alkyl substituted phenyl ($C_1$-$C_{20}$)alkyl, mono($C_1$-$C_{20}$)alkoxy substituted phenyl($C_1$-$C_{20}$)alkyl, ($C_1$-$C_{20}$)alkoxy($C_2$-$C_{20}$)alkyl, $C_3$-$C_{10}$ cycloalkyl, or mono($C_1$-$C_{20}$)alkyl substituted $C_3$-$C_{10}$ cycloalkyl; —N($R_{11}$')$R_{12}$', wherein $R_{11}$' and $R_{12}$' are each independently hydrogen, $C_1$-$C_{20}$ alkyl, phenyl, naphthyl, furanyl, benzofuran-2-yl, benzofuran-3-yl, thienyl, benzothien-2-yl, benzothien-3-yl, dibenzofuranyl, dibenzothienyl, benzopyridyl, fluorenyl, $C_1$-$C_{20}$ alkylaryl, $C_3$-$C_{10}$ cycloalkyl, $C_4$-$C_{20}$ bicycloalkyl, $C_5$-$C_{20}$ tricycloalkyl or $C_1$-$C_{20}$ alkoxyalkyl, wherein said aryl group is phenyl or naphthyl, or $R_{11}$' and $R_{12}$' come together with the nitrogen atom to form a $C_3$-$C_{20}$ hetero-bicycloalkyl ring or a $C_4$-$C_{20}$ hetero-tricycloalkyl ring;

a nitrogen containing ring represented by the following graphic formula XIIA,

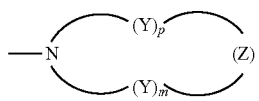

XIIA wherein each —Y— is independently chosen for each occurrence from —$CH_2$—, —CH($R_{13}$')—, —C($R_{13}$')$_2$—, —CH(aryl)-, —C(aryl)$_2$-, and —C($R_{13}$')(aryl)-, and Z is —Y—, —O—, —S—, —S(O)—, —SO$_2$—, —NH—, —N($R_{13}$')—, or —N(aryl)-, wherein each $R_{13}$' is independently $C_1$-$C_{20}$ alkyl, each aryl is independently phenyl or naphthyl, m is an integer 1, 2 or 3, and p is an integer 0, 1, 2, or 3 and provided that when p is 0, Z is —Y—;

a group represented by one of the following graphic formulae XIIB or XIIC,

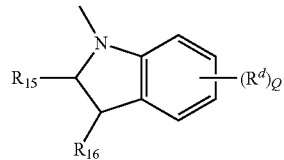

XIIB

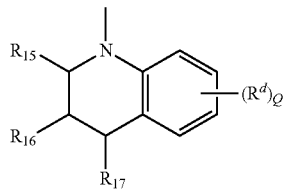

XIIC wherein $R_{15}$, $R_{16}$, and $R_{17}$ are each independently hydrogen, $C_1$-$C_{20}$ alkyl, phenyl, or naphthyl, or the groups $R_{15}$ and $R_{16}$ together form a ring of 5 to 8 carbon atoms and each $R^d$ is independently for each occurrence selected from $C_1$-$C_{20}$ alkyl, $C_1$-$C_{20}$ alkoxy, fluoro or chloro, and Q is an integer 0, 1, 2, or 3; and unsubstituted, mono-, or di-substituted $C_4$-$C_{18}$ spirobicyclic amine, or unsubstituted, mono-, and di-substituted $C_4$-$C_{18}$ spirotricyclic amine, wherein said substituents are independently aryl, $C_1$-$C_6$ alkyl, $C_1$-$C_6$ alkoxy, or phenyl($C_1$-$C_{20}$)alkyl; or two adjacent $R^1$ groups, or two adjacent $R^2$ groups, independently together form a group represented by one of XIID and XIIE:

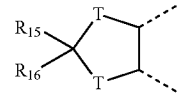

XIID

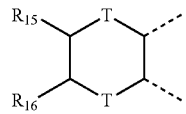

XIIE wherein T and T' are each independently oxygen or the group —N$R_{11}$'—, where $R_{11}$', $R_{15}$, and $R_{16}$ are as set forth above; and $R^3$ and $R^4$ are each independently selected from, (i) hydrogen, $C_1$-$C_{20}$ alkyl, $C_1$-$C_{20}$ haloalkyl, $C_3$-$C_{10}$ cycloalkyl, allyl, benzyl, or mono-substituted benzyl, said benzyl substituents being chosen from halogen, $C_1$-$C_{20}$ alkyl or $C_1$-$C_{20}$ alkoxy;

(ii) an unsubstituted, mono- di- or tri-substituted group chosen from phenyl, naphthyl, phenanthryl, pyrenyl, quinolyl, isoquinolyl, benzofuranyl, thienyl, benzothienyl, dibenzofuranyl, dibenzothienyl, carbazolyl, or indolyl, said group substituents in being chosen from halogen, $C_1$-$C_{20}$ alkyl or $C_1$-$C_{20}$ alkoxy;

(iii) mono-substituted phenyl, said substituent located at the para position being —($CH_2$)$_t$— or —O—($CH_2$)$_t$—, wherein t is the integer 1, 2, 3, 4, 5 or 6, said substituent being connected to an aryl group which is a member of a photochromic material;

(iv) the group —CH($R^{10}$)G, wherein $R^{10}$ is hydrogen, $C_1$-$C_{20}$ alkyl or the unsubstituted, mono- or di-substituted aryl groups phenyl or naphthyl, and G is —CH$_2$OR$^{11}$, wherein R$^{11}$ is hydrogen, —C(O)R$^{10}$, C$_1$-C$_{20}$ alkyl, C$_1$-C$_{20}$ alkoxy(C$_1$-C$_{20}$)alkyl, phenyl (C$_1$-C$_{20}$)alkyl, mono(C$_1$-C$_{20}$)alkoxy substituted phenyl(C$_1$-C$_{20}$)alkyl, or the unsubstituted, mono- or di-substituted aryl groups phenyl or naphthyl, each of said phenyl and naphthyl group substituents being C$_1$-C$_{20}$ alkyl or C$_1$-C$_{20}$ alkoxy; and B and B' are each independently:
an aryl group that is mono-substituted with a reactive substituent or a compatiblizing substituent; a substituted phenyl; a substituted aryl; a substituted 9-julolindinyl; a substituted heteroaromatic group chosen from pyridyl, furanyl, benzofuran-2-yl, benzofuran-3-yl, thienyl, benzothien-2-yl, benzothien-3-yl, dibenzofuranyl, dibenzothienyl, carbazoyl, benzopyridyl, indolinyl, and fluorenyl, wherein the phenyl, aryl, 9-julolindinyl, or heteroaromatic substituent is the reactive substituent R; an unsubstituted, mono-, di-, or tri-substituted phenyl or aryl group; 9-julolidinyl; or an unsubstituted, mono- or di-substituted heteroaromatic group chosen from pyridyl, furanyl, benzofuran-2-yl, benzofuran-3-yl, thienyl, benzothien-2-yl, benzothien-3-yl, dibenzofuranyl, dibenzothienyl, carbazoyl, benzopyridyl, indolinyl, and fluorenyl, wherein each of the phenyl, aryl and heteroaromatic substituents are each independently:
hydroxyl, a group —C(═O)R$_{21}$, wherein R$_{21}$ is —OR$_{22}$, —N(R$_{23}$)R$_{24}$, piperidino, or morpholino, wherein R$_{22}$ is allyl, C$_1$-C$_{20}$ alkyl, phenyl, mono(C$_1$-C$_{20}$)alkyl substituted phenyl, mono(C$_1$-C$_{20}$)alkoxy substituted phenyl, phenyl(C$_1$-C$_{20}$)alkyl, mono(C$_1$-C$_{20}$)alkyl substituted phenyl(C$_1$-C$_{20}$)alkyl, mono (C$_1$-C$_{20}$)alkoxy substituted phenyl (C$_1$-C$_{20}$)alkyl, C$_1$-C$_{20}$ alkoxy(C$_2$-C$_{20}$)alkyl or C$_1$-C$_{20}$ haloalkyl, R$_{23}$ and R$_{24}$ are each independently C$_1$-C$_{20}$ alkyl, C$_5$-C$_{10}$ cycloalkyl, phenyl or substituted phenyl, the phenyl substituents being C$_1$-C$_{20}$ alkyl or C$_1$-C$_{20}$ alkoxy, and said halo substituent is chloro or fluoro, aryl, mono(C$_1$-C$_{20}$)alkoxyaryl, di(C$_1$-C$_{20}$)alkoxyaryl, mono(C$_1$-C$_{20}$)alkylaryl, di(C$_1$-C$_{20}$)alkylaryl, haloaryl, C$_3$-C$_{10}$ cycloalkylaryl, C$_3$-C$_{10}$ cycloalkyl, C$_3$-C$_{10}$ cycloalkyloxy, C$_3$-C$_{10}$ cycloalkyloxy(C$_1$-C$_{20}$)alkyl, C$_3$-C$_{10}$ cycloalkyloxy(C$_1$-C$_{20}$)alkoxy, aryl(C$_1$-C$_{20}$)alkyl, aryl(C$_1$-C$_{20}$)alkoxy, aryloxy, aryloxy(C$_1$-C$_{20}$)alkyl, aryloxy(C$_1$-C$_{20}$)alkoxy, mono- or di(C$_1$-C$_{20}$)alkylaryl(C$_1$-C$_{20}$)alkyl, mono- or di-(C$_1$-C$_{20}$)alkoxyaryl(C$_1$-C$_{20}$)alkyl, mono- or di-(C$_1$-C$_{20}$)alkylaryl(C$_1$-C$_{20}$)alkoxy, mono- or di-(C$_1$-C$_{20}$) alkoxyaryl(C$_1$-C$_{20}$)alkoxy, amino, mono- or di-(C$_1$-C$_{20}$)alkylamino, diarylamino, piperazino, N—(C$_1$-C$_{20}$)alkylpiperazino, N-arylpiperazino, aziridino, indolino, piperidino, morpholino, thiomorpholino, tetrahydroquinolino, tetrahydroisoquinolino, pyrrolidyl, C$_1$-C$_{20}$ alkyl, C$_1$-C$_{20}$ haloalkyl, C$_1$-C$_{20}$ alkoxy, mono(C$_1$-C$_{20}$)alkoxy(C$_1$-C$_{20}$)alkyl, acryloxy, methacryloxy, or halogen;
an unsubstituted or mono-substituted group chosen from pyrazolyl, imidazolyl, pyrazolinyl, imidazolinyl, pyrrolinyl, phenothiazinyl, phenoxazinyl, phenazinyl, and acridinyl, each of said substituents being C$_1$-C$_{20}$ alkyl, C$_1$-C$_{20}$ alkoxy, phenyl, or halogen;

a group represented by one of:

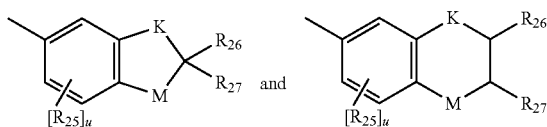

wherein K is —CH$_2$— or —O—, and M is —O— or substituted nitrogen, provided that when M is substituted nitrogen, K is —CH$_2$—, the substituted nitrogen substituents being hydrogen, C$_1$-C$_{20}$ alkyl, or C$_1$-C$_{20}$ acyl, each R$_{25}$ being independently chosen for each occurrence from C$_1$-C$_{20}$ alkyl, C$_1$-C$_{20}$ alkoxy, hydroxy, and halogen, R$_{26}$ and R$_{27}$ each being independently hydrogen or C$_1$-C$_{20}$ alkyl, and u is an integer ranging from 0 to 2; or a group represented by:

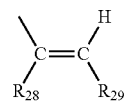

wherein R$_{28}$ is hydrogen or C$_1$-C$_{20}$ alkyl, and R$_{29}$ is an unsubstituted, mono-, or di-substituted group chosen from naphthyl, phenyl, furanyl, and thienyl, wherein the substituents are C$_1$-C$_{20}$ alkyl, C$_1$-C$_{20}$ alkoxy, or halogen; or B and B' taken together form one of a fluoren-9-ylidene, mono-, or di-substituted fluoren-9-ylidene, each of said fluoren-9-ylidene substituents being independently chosen from C$_1$-C$_{20}$ alkyl, C$_1$-C$_{20}$ alkoxy, and halogen.

3. The method of claim 2, wherein,
R$^1$ for each m, and R$^2$ for each n, are in each case independently selected from C$_1$-C$_6$ alkyl, C$_3$-C$_7$ cycloalkyl, C$_1$-C$_8$ haloalkyl, fluoro, chloro, and —O—R$_{10}$',
R$^3$ and R$^4$ are each independently selected from hydrogen, C$_1$-C$_8$ alkyl, C$_1$-C$_8$ haloalkyl, and C$_3$-C$_7$ cycloalkyl, and
B and B' are each independently selected from aryl substituted with C$_1$-C$_6$ alkoxy, and aryl substituted with morpholine.

4. The method of claim 1, wherein said A and B ring fused indenopyran compound is represented by the following Formula XVa,

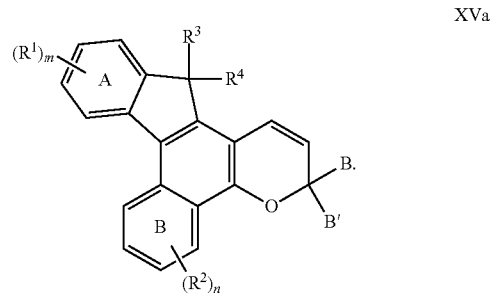

5. The method of claim 4, wherein,
said unsaturated compound represented by Formula II, is represented by Formula IIb, IIb

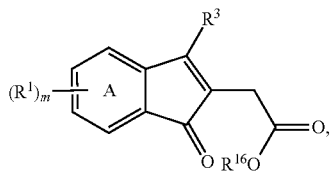

said saturated compound represented by Formula IV, is represented by Formula IVb, IVb

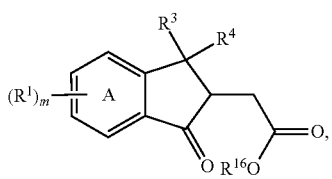

said second nucleophile represented by Formula V, is represented by Formula Va,

Va

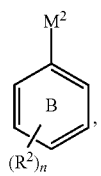

and
said substituted intermediate represented by at least one of Formula VI, Formula VII and Formula VIII, is represented by at least one of Formula VIb, Formula VIIb and Formula VIIIb, VIb

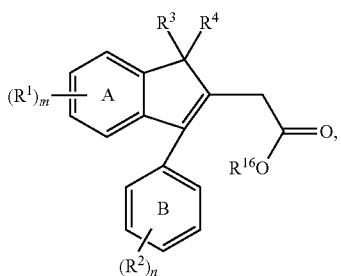

VIIb

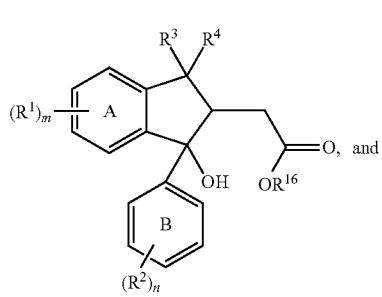

, and

VIIIb

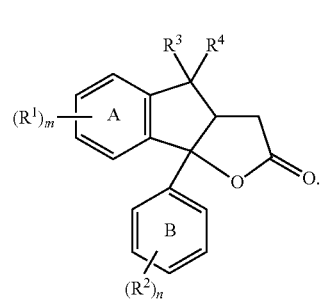

.

* * * * *